(12) United States Patent
Fischer et al.

(10) Patent No.: US 6,476,296 B1
(45) Date of Patent: Nov. 5, 2002

(54) NUCLEIC ACIDS THAT CONTROL SEED AND FRUIT DEVELOPMENT IN PLANTS

(75) Inventors: Robert L. Fischer, El Cerrito, CA (US); Yeonhee Choi, Emeryville, CA (US); Mike Hannon, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/553,690

(22) Filed: Apr. 21, 2000

(51) Int. Cl.$^7$ .............................. A01H 5/00; C12N 5/04; C12N 5/10; C12N 15/29; C12N 15/82

(52) U.S. Cl. ...................... 800/290; 800/286; 800/266; 800/294; 800/298; 435/469; 435/419; 435/468; 435/320.1; 435/69.8; 536/23.6

(58) Field of Search .............................. 536/23.6, 24.1; 800/290, 298, 286, 266, 294; 435/468, 419, 69.8, 469, 320.1

(56) References Cited

PUBLICATIONS

Akama, K. et al., "Efficient transformation of *Arabidopsis thalian*: comparison of the efficiencies with various organs, plant ecotypes and Agrobacterium strains." 1992, Plant Cell Reports, vol. 12, pp. 7–11.*
Hill, M. A. and Preiss, J. "Functional Analysis of Conserved Histidines in ADP–Glucose Pyrophosphorylase from *Escherichia coli*." 1998, Biochemical and Biophysical Res. Comm., vol. 244, pp. 573–577.*
Broun, P. et al., "Catalytic Plasticity of Fatty Acid Modification Enzymes Underlying Chemical Diversity of Plant Lipids." 1998, Science, vol. 282, pp. 1315–1317.*
Bowie, J. U. et al., "Deciphering the Message in Protein Sequences: Tolerance to Amino Acid Substitutions." 1990, Science, vol. 247, pp. 1306–1310.*
Lazar, E. et al., "Transforming Growth Factor a: Mutation of Aspartic Acid 47 and Leucine 48 Results in Different Biological Activities." 1988, Molecular and Cellular Biology, vol. 8, pp. 1247–1252.*
Bevan, M. et al., Accession No. AL162875, Mar. 31, 2000.*
Bork, C. et al., Accession No. Y10157, Jul. 1, 1998.*
Bork, C. et al., "Isolation and characterization of a gene for assimilatory sulfite reductase from *Arabidopsis thaliana*." 1998, Gene, vol. 212, pp. 147–153.*
Bult, C. J. et al., Accession No. Q58030, Nov. 1, 1997.*
Smith, D. R. et al., Accession No. AE000855, AE000666, Nov. 15, 1997.*
White, O. et al., Accession No. AE002073, AE000513, Nov. 22, 1999.*
Colliver, S. P. et al., "Differential modification of flavonoid and isoflavonoid biosynthesis with an antisense chalcone synthase construct in transgenic Lotus corniculatus." 1997, Plant Molecular Biology, vol. 35, pp. 509–522.*
van der Krol, A. et al., "Inhibition of flower pigmentation by antisense CHS genes: promoter and minimal sequence requirements for the antisense effect." 1990, Plant Molecular Biology, vol. 14, pp. 457–466.*
Klann, E. M. et al., "Antisense Acid Invertase (TIV1) Gene Alters Soluble Sugar Composition and Size in Transgenic Tomato Fruit." 1996, Plant Physiol., vol. 112, pp. 1321–1330.*
Kuipers, A. G. J. et al., "Factors affecting the inhibition by antisense RNA of granule–bound starch synthase gene expression in potato." 1995, Mol Gen Genet, vol. 246, pp. 745–755.*
Bird, C. R. et al., "Using Antisense RNA to Study Gene Function: Inhibition of Carotenoid Biosynthesis in Transgenic Tomatoes." 1991, Bio/Technology, vol. 9, pp. 635–639.*
Tang, G. et al., "Antisense Repression of Vacuolar and Cell Wall Invertase in Transgenic Carrot Alters Early Plant Development and Sucrose Partitioning." 1999, The Plant Cell, vol. 11, pp. 177–189.*
Robbins, M. P. et al., "Genetic Manipulation of Condensed Tannins in Higher Plants." 1998, Plant Physiol., vol. 116, pp. 1133–1144.*
Elomaa, P. et al., "Transformation of antisense constructs of the chalcone synthase gene superfamily into *Gerbera hybida*: differential effect on the expression of family members." 1996, Molecular Breeding, vol. 2, pp. 41–50.*
Luo, M. et al., "Genes controlling fertilization–independent seed development in *Arabidopsis thaliana*." 1999, Proc. Natl. Acad. Sci. USA, vol. 96, pp. 296–301.*
Kiyosue, T. et al., "Control of fertilization–independent endosperm development by the Medea polycomb gene in Arabidopsis." 1999, Proc. Natl. Acad. Sci. USA, vol. 96, pp. 4186–4191.*
Ohad, N. et al., "A mutation that allows endosperm development without fertilization." 1996, Proc. Natl. Acad. Sci. USA, vol. 93, pp. 5319–5324.*
Roldan–Arjona, T. et al., "cDNA cloning, expression and functional characterization of an *Arabidopsis thaliana* homologue of the *Escherichia coli* DNA repair enzyme endonuclease III." 2000, Plant Molecular Biology, vol. 44, pp. 43–52.*

* cited by examiner

Primary Examiner—David T. Fox
Assistant Examiner—Anne Kubelik
(74) Attorney, Agent, or Firm—Townsend and Townsend and Crew LLP

(57) ABSTRACT

The invention provides methods of controlling endosperm and seed development in plants.

38 Claims, No Drawings

US 6,476,296 B1

NUCLEIC ACIDS THAT CONTROL SEED AND FRUIT DEVELOPMENT IN PLANTS

STATEMENT AS TO RIGHTS TO INVENTIONS MADE UNDER FEDERALLY SPONSORED RESEARCH AND DEVELOPMENT

This invention was made with Government support under Grant No. 97-35304-4941, awarded by the United States Department of Agriculture. The government has certain rights in this invention.

FIELD OF THE INVENTION

This invention is directed to plant genetic engineering. In particular, it relates to modulating seed (and in particular endosperm, embryo and seed coat) development in plants.

BACKGROUND OF THE INVENTION

A fundamental problem in biology is to understand how seed development. In flowering plants, the ovule generates the female gametophyte which is composed of egg, central, synergid and antipodal cells (Reiser, et al., *Plant Cell*, 1291–1301 (1993)). All are haploid except the central cell which contains two daughter nuclei that fuse prior to fertilization. One sperm nucleus fertilizes the egg to form the zygote, whereas another sperm nucleus fuses with the diploid central cell nucleus to form the triploid endosperm nucleus (van Went, et al., *Embryology of Angiosperms*, pp. 273–318 (1984)). The two fertilization products undergo distinct patterns of development. In Arabidopsis, the embryo passes through a series of stages that have been defined morphologically as preglobular, globular, heart, cotyledon and maturation (Goldberg, R. B., et al., *Science* (1994) 266: 605–614; Mansfield, S. G., et al., *Arabidopsis: An Atlas of Morphology and Development*, pp. 367–383 (1994)). The primary endosperm nucleus undergoes a series of mitotic divisions to produce nuclei that migrate into the expanding central cell (Mansfield, S. G., et al., *Arab Inf Serv* 27: 53–64 (1990); Webb, M. C., et al., *Planta* 184:187–195 (1991)). Cytokinesis sequesters endosperm cytoplasm and nuclei into discrete cells (Mansfield, S. G., et al., *Arab Inf Serv* 27:65–72 (1990)) that produce storage proteins, starch, and lipids which support embryo growth (Lopes, M. A. et al., *Plant Cell* 5:1383–1399 (1993)). Fertilization also activates development of the integument cell layers of the ovule that become the seed coat, and induces the ovary to grow and form the fruit, or silique, in Arabidopsis.

Of particular interest are recent discoveries of genes that control seed, and in particular endosperm, development. For instance, MEDEA (MEA) (also known as FIE1 (see, e.g., copending U.S. patent application Ser. No. 09/071,838) and F644 (see, e.g., Kiyosue T, et al. (1 999) *Proc Natl Acad Sci USA* 96(7):4186–91) encodes an Arabidopsis SET domain polycomb protein that appears to play a role in endosperm development. Inheritance of a maternal loss-of-function mea allele results in embryo abortion and prolonged endosperm production, irrespective of the genotype of the paternal allele. Thus, only the maternal wild-type MEA allele is required for proper embryo, endosperm, and seed coat development (Kinoshita T, et al. (1999) *Plant Cell* 10:1945–52). These results reveal functions for plant polycomb proteins in the suppression of central cell proliferation and endosperm development (Kiyosue T, et al. supra).

Another gene product that controls seed development is FIE, also known as FIE3 (see, e.g., copending U.S. patent application Ser. No. 09/071,838). The FIE protein is a homolog of the WD motif-containing Polycomb proteins from Drosophila and mammals (Ohad, N. et al. *Plant Cell* 11(3):407–16 (1999)). In Drosophila, these proteins function as repressors of homeotic genes. A female gametophyte with a loss-of-function allele of fie undergoes replication of the central cell nucleus and initiates endosperm development without fertilization. These results suggest that the FIE Polycomb protein functions to suppress a critical aspect of early plant reproduction, namely, endosperm development, until fertilization occurs.

Control of the expression of genes that control egg and central cell differentiation, or those that control reproductive development, i.e. embryo, endosperm and seed coat, is useful in the production of plants with a range of desired traits. These and other advantages are provided by the present application.

SUMMARY OF THE INVENTION

This invention provides isolated nucleic acids comprising a polynucleotide sequence, or its complement, encoding an ATR polypeptide exhibiting at least 60% sequence identity to SEQ ID NO:2. For instance, the nucleic acid can encode the ATR polypeptide displayed in SEQ ID NO:2. In one aspect, the polynucleotide sequence comprises SEQ ID NO:5 or SEQ ID NO:1. In some aspects of the invention, the nucleic acid further comprises a promoter operably linked to the polynucleotide. In some embodiments, the promoter is constitutive. In other embodiments, the promoter is from an ATR gene. For example, the promoter can comprise a polynucleotide at least 70% identical to SEQ ID NO:3. In some aspects, the promoter comprises SEQ ID NO:3. In some aspects of this invention, the promoter further comprises a polynucleotide at least 70% identical to SEQ ID NO:4. For example, in some aspects the promoter comprises SEQ ID NO:4. In some aspects, the polynucleotide sequence is linked to the promoter in an antisense orientation.

The invention also provides an isolated nucleic acid molecule comprising a polynucleotide sequence exhibiting at least 60% sequence identity to SEQ ID NO:1.

The invention also provides an expression cassette comprising a promoter operably linked to a heterologous polynucleotide sequence, or complement thereof, encoding an ATR polypeptide exhibiting at least 60% sequence identity to SEQ ID NO:2. For instance, the nucleic acid can encode the ATR polypeptide displayed in SEQ ID NO:2. In some aspects, the polynucleotide sequence comprises SEQ ID NO:5 or SEQ ID NO:1. In some aspects of the invention, the nucleic acid further comprises a promoter operably linked to the polynucleotide. In some embodiments, the promoter is constitutive. In other embodiments, the promoter is from an ATR gene. For example, the promoter can comprise a polynucleotide at least 70% identical to SEQ ID NO:3. In some aspects, the promoter comprises SEQ ID NO:3. In some aspects of this invention, the promoter further comprises a polynucleotide at least 70% identical to SEQ ID NO:4. For example, in some aspects the promoter comprises SEQ ID NO:4. In some aspects, the polynucleotide sequence is linked to the promoter in an antisense orientation.

The invention also provides an expression cassette for the expression of a heterologous polynucleotide in a plant cell. In some aspects, the expression cassette comprises a promoter polynucleotide at least 70% identical to SEQ ID NO:3 that is operably linked to a heterologous polynucleotide. In some aspects, the promoter comprises SEQ ID NO:3. In some aspects, the promoter further comprises a polynucleotide at least 70% identical to SEQ ID NO:4. For instance, in some embodiments, the promoter comprises SEQ ID NO:4.

The present invention also provides a host cell comprising an exogenous polynucleotide sequence comprising a polynucleotide sequence, or complement thereof, encoding an ATR polypeptide exhibiting at least 60% sequence identity to SEQ ID NO:2. In some aspects of the invention, the nucleic acid further comprises a promoter operably linked to the polynucleotide sequence. In some aspects, the promoter is constitutive. In some aspects, the promoter comprises a polynucleotide at least 70% identical to SEQ ID NO:3. The promoter, for instance, can comprise SEQ ID NO:3. In some aspects, the promoter further comprises a polynucleotide at least 70% identical to SEQ ID NO:4. For instance, in some embodiments, the promoter comprises SEQ ID NO:4. In some aspects, the promoter is operably linked to the exogenous polynucleotide sequence in an antisense orientation.

The present invention also provides an isolated polypeptide comprising an amino acid sequence at least 60% identical to SEQ ID NO:2 and capable of exhibiting at least one biological activity of the polypeptide displayed in SEQ ID NO:2, or fragment thereof. The present invention also provides for an antibody capable of binding such polypeptides.

The present invention also provides a method of introducing an isolated nucleic acid into a host cell comprising, (a) providing an isolated nucleic acid or its complement, encoding an ATR polypeptide exhibiting at least 60% sequence identity to SEQ ID NO:2. and (b) contacting the nucleic acid with the host cell under conditions that permit insertion of the nucleic acid into the host cell.

The present invention also provides a method of modulating transcription, comprising introducing into a host cell an expression cassette comprising a promoter operably linked to a heterologous ATR polynucleotide, the heterologous ATR polynucleotide encoding an ATR polypeptide at least 60% identical to SEQ ID NO:2, and detecting a host cell with modulated transcription. In some aspects of the invention, the heterologous ATR polynucleotide encodes SEQ ID NO:2. In some aspect, the polynucleotide sequence comprises SEQ ID NO:5 or SEQ ID NO:1. In some aspects, the expression cassette is introduced into a host cell by Agrobacterium. In some aspects, the expression cassette is introduced by a sexual cross. In some aspects of the method of the invention, modulating transcription results in the modulation of endosperm development in a plant. In some aspects, endosperm development is enhanced. In other aspects, endosperm development is decreased. In some aspects of the methods of the invention, the promoter is operably linked to the ATR polynucleotide in an antisense orientation.

The present invention also provides a method of detecting a nucleic acid in a sample, comprising (a) providing an isolated nucleic acid molecule comprising a polynucleotide sequence, or its complement, encoding a R polypeptide exhibiting at least 60% sequence identity to SEQ ID NO:2., (b) contacting the isolated nucleic acid molecule with a sample under conditions that permit a comparison of the sequence of the isolated nucleic acid molecule with the sequence of DNA in the sample, and (c) analyzing the result of the comparison. In some aspects of the method, the isolated nucleic acid molecule and the sample are contacted under conditions that permit the formation of a duplex between complementary nucleic acid sequences.

The present invention also provides a transgenic plant cell or transgenic plant comprising a polynucleotide sequence, or its complement, encoding an ATR polypeptide exhibiting at least 60% sequence identity to SEQ ID NO:2. For instance, the nucleic acid can encode the ATR polypeptide displayed in SEQ ID NO:2. In one aspect, the polynucleotide sequence comprises SEQ ID NO:5 or SEQ ID NO:1. In some aspects of the invention, the nucleic acid further comprises a promoter operably linked to the polynucleotide. In some embodiments, the promoter is constitutive. In other embodiments, the promoter comprises a polynucleotide at least 70% identical to SEQ ID NO:3. In some aspects, the promoter comprises SEQ ID NO:3. In some aspects of this invention, the promoter further comprises a polynucleotide at least 70% identical to SEQ ID NO:4. For example, in some aspects the promoter comprises SEQ ID NO:4. In some aspects, the polynucleotide sequence is linked to the promoter in an antisense orientation. The present invention also provides a plant that is regenerated from a plant cell as described above.

DEFINITIONS

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

A "promoter" is defined as an array of nucleic acid control sequences that direct transcription of an operably linked nucleic acid. As used herein, a "plant promoter" is a promoter that functions in plants. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, plant organs (e.g., leaves, stems, flowers, roots, etc.), seeds and plant cells and progeny of same. The class of plants which can be used in the method of the invention is generally as broad as the class of flowering plants amenable to transformation techniques, including angiosperms (monocotyledonous and dicotyledonous plants), as well as gymnosperms. It includes plants of a variety of ploidy levels, including polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant, or a predecessor generation of the plant, by any means other than by a sexual cross. Examples of means by which this can be accomplished are described below, and include Agrobacterium-mediated transformation, biolistic methods, electroporation, in planta techniques, and the like.

The phrase "host cell" refers to a cell from any organism. Preferred host cells are derived from plants, bacteria, yeast, fungi, insects or other animals. Methods for introducing polynucleotide sequences into various types of host cells are well known in the art.

The "biological activity of a polypeptide" refers to any molecular activity or phenotype that is caused by the polypeptide. For example, the ability to transfer a phosphate to a substrate or the ability to bind a specific DNA sequence is a biological activity. One biological activity of ATR is the ability to modulate endosperm production in plants.

An "expression cassette" refers to a nucleic acid construct, which when introduced into a host cell, results in transcription and/or translation of an RNA or polypeptide, respectively. Antisense or sense constructs that are not or cannot be translated are expressly included by this definition.

A "ATR nucleic acid" or "ATR polynucleotide sequence" of the invention is a subsequence or full length polynucleotide sequence of a gene which encodes a polypeptide involved in control of reproductive development and which, when the maternal allele is mutated, allows for increased production of the endosperm and/or abortion of the embryo. In some embodiments, the polypeptides of the invention have a nuclear localization signal. An exemplary nucleic acid of the invention is the Arabidopsis ATR sequence disclosed below. ATR polynucleotides are defined by their ability to hybridize under defined conditions to the exemplified nucleic acids or PCR products derived from them. An ATR polynucleotide is typically at least about 30–40 nucleotides to about 7000, usually less than about 10000 nucleotides in length. The nucleic acids contain coding sequence of from about 100 to about 4000 nucleotides, often from about 500 to about 3600 nucleotides in length.

ATR nucleic acids are a new class of plant regulatory genes that encode polypeptides with sequence identity to members of the endonuclease III genes found in a diverse collection of organisms. Endonuclease III is implicated in various DNA repair reactions. Thus proteins related to endonuclease III are likely to have a chromosomal function. ATR (SEQ ID NO:1) is most related to endonuclease III from *Deinococcus radiodurans* Genbank Accession No. AE002073 (see, e.g., White, O. et al. *Science* 286:1571–1577 (1999)). ATR polynucleotides can also encode abipartite nuclear localization signal (e.g., amino acid positions 43–60 and 61–78 in SEQ ID NO:2) comprised of basic amino acids. ATR polypeptides also contain a leucine zipper sequence (e.g., positions 1330–1351 of SEQ ID NO:2).

In the case of both expression of transgenes and inhibition of endogenous genes (e.g., by antisense, or sense suppression) one of skill will recognize that the inserted polynucleotide sequence need not be identical, but may be only "substantially identical" to a sequence of the gene from which it was derived. As explained below, these substantially identical variants are specifically covered by the term ATR nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "ATR nucleic acid". In addition, the term specifically includes those sequences substantially identical (determined as described below) with an ATR polynucleotide sequence disclosed here and that encode polypeptides that are either mutants of wild type ATR polypeptides or retain the function of the ATR polypeptide (e.g., resulting from conservative substitutions of amino acids in the ATR polypeptide). In addition, variants can be those that encode dominant negative mutants as described below.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to a sequence or subsequence that has at least 40% sequence identity with a reference sequence. Alternatively, percent identity can be any integer from 40% to 100%. More preferred embodiments include at least: 40%, 45%, 50%, 55%, 60%, 65%, 70%, 75%, 80%, 85%, 90%, 95%, or 99%. compared to a reference sequence using the programs described herein; preferably BLAST using standard parameters, as described below. This definition also refers to the complement of a test sequence, when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. MoL Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing finctionally similar amino acids are well known in the art.

The following six groups each contain amino acids that are conservative substitutions for one another:

1) Alanine (A), Serine (S), Threonine (T);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V); and

6) Phenylalanine (F), Tyrosine (Y), Tryptophan (W). (see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5–10° C. lower than the thermal melting point ($T_m$) for the specific sequence at a defmed ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as fonnamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

In the present invention, genomic DNA or cDNA comprising ATR nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

DETAILED DESCRIPTION

This invention provides molecular strategies for controlling seed and fruit development, and in particular, endosperm development.

Reproduction in flowering plants involves two fertilization events in the haploid female gametophyte. One sperm nucleus fertilizes the egg to form the embryo. A second sperm nucleus fertilizes the central cell to form the endosperm, a unique tissue that supports the growth of the embryo. Fertilization also activates maternal tissue differentiation, the ovule integuments form the seed coat and the ovary forms the fruit.

The present invention is based, at least in part, on the discovery of a set of female-gametophytic mutations and the subsequent cloning of the gene, termed ATROPOS (ATR), involved. Two mutant alleles of ATR disclosed here were created using a T-DNA tag, thereby disrupting an exon of the gene. The atr mutations affect endosperm production, allowing for increased endosperm development. Generally, the mutant atr alleles are not transmitted by the female gametophyte. Inheritance of a mutant atr allele by the female gametophyte usually results in embryo abortion and endosperm overproduction, even when the pollen bears the wild-type ATR allele.

In contrast, transmission of atr mutant alleles through the male gametophyte (i.e., pollen) is ecotype-dependent in Arabidopsis. For instance, in some ecotypes (e.g., Columbia), transmission of atr mutant alleles is less than 50%. However, in Landsberg erecta, transmission is almost normal.

The isolated sequences prepared as described herein, can be used in a number of techniques, for example, to suppress or enhance endogenous ATR gene expression. Modulation of ATR gene expression or ATR activity in plants is particularly useful, for example, in producing embryo-less or embryo-reduced seed, seed with increased endosperm, or as part of a system to generate seed.

Isolation of ATR Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989).

The isolation of ATR nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as ovules, and a cDNA library which contains the ATR gene transcript is prepared from the mRNA. Alternatively, cDNA may be prepared from mRNA extracted from other tissues in which ATR genes or homologs are expressed.

The cDNA or genomic library can then be screened using a probe based upon the sequence of a cloned ATR gene disclosed here. Probes may be used to hybridize with genomic DNA or cDNA sequences to isolate homologous genes in the same or different plant species. Alternatively, antibodies raised against an ATR polypeptide can be used to screen an mRNA expression library.

Alternatively, the nucleic acids of interest can be amplified from nucleic acid samples using amplification techniques. For instance, polymerase chain reaction (PCR) technology can be used to amplify the sequences of the ATR genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see PCR Protocols: *A Guide to Methods and Applications*. (Innis, M, Gelfand, D., Sninsky, J. and White, T., eds.), Academic Press, San Diego (1990).

Appropriate primers and probes for identifying A TR sequences from plant tissues are generated from comparisons of the sequences provided here with other related genes. For instance, ATR can be compared to the other endonuclease III genes, such as Genbank Accession No. AE002073. Using these techniques, one of skill can identify conserved regions in the nucleic acids disclosed here to prepare the appropriate primer and probe sequences. Primers that specifically hybridize to conserved regions in ATR genes can be used to amplify sequences from widely divergent plant species. Appropriate primers for amplification of the genomic region or cDNA of LEC2 include the following primers:

Xba-SKEN-7; CCTCTAGAGGAATTGTCG-GCAAAATCGAG (SEQ ID NO:7)

SKB-8; GGAGAGACGGTTATTGTCAACC (SEQ ID NO:8)

SKB-7; AAAAGTCTACAAGGGAGAGAGAGT (SEQ ID NO:9)

SKB-5; GTAGATGTACATACGTACC (SEQ ID NO10)

SKEN-8; GCATCCTCCAACAAGTAACAATCCACTC (SEQ ID NO:11)

SKB-6; CACTGAGATTAATTCTTCAGACTCG (SEQ ID NO:12)

SKEN-3.5; CTCAGGCGAGTCAATGCCGGAGAA-CAC (SEQ ID NO:13)

SKEN-3; CGAGGGCTGATCCGGGGGATA-GATATTTT (SEQ ID NO:14)

SKEN-2; CCCCCGGATCAGCCCTCGAATTC (SEQ ID NO:15)

SKEN-1;CCCCTGTCTACAAATTCACCACCTGG (SEQ ID NO:16)

SKEL-4; CTGACCCAACTGCTTCTCTTC (SEQ ID NO:17)

skes1.5; TCACCTGTTCTGAACAGACTGG (SEQ ID NO:18)

SKES-1.4; CAGCAGACGAGTCCATAATGCTCTGC (SEQ ID NO:19)

SKES-2.4; GGTTTGCCTTCCACGACCACC (SEQ ID NO:20)

SKES-1; GGAAGCCACGCAAAGCTGCAACTCAGG (SEQ ID NO:21)

SKES-2.45; GAGTTGCAGCTTTGCGTGGCTTCC (SEQ ID NO:22)

SKES2.5; TTCAGACTCAGAGTCACCTTGC (SEQ ID NO:23)

SKES-2; ACCAGCAGCCTTGCTTGGCC (SEQ ID NO:24)

SKES-3; CATGCCAGAGAAGCAGGGCTCC (SEQ ID NO:25)

SKES3.5; CGATGATACTGTCTCTTCGAGC (SEQ ID NO:26)

SKES-6; CCTCCGCCTGCTCATGCCTCAG (SEQ ID NO:27)

SKEN-4; GTCCATCAGGAGAACTTCTGTGTCAG-GAT (SEQ ID NO:28)

SKES-4; GGGAACAAGTGCACCATCTCC (SEQ ID NO:29)

SKEN-6; GCTCTCATAGGGAACAAGTGCAC-CATCTC (SEQ ID NO:30)

SKES-5; CGCTCGCATGCACCTGGTAC (SEQ ID NO:31)

SKB-1;GGAGGGAATCGAGCAGCTAGAG (SEQ ID NO:32)

SKB-2; GAGCAGCTAAGGGACTGTTCAAACTC (SEQ ID NO:33)

SKB-3; CCAGGAATGGGATTGTCCGG (SEQ ID NO:34)

3'RACE-2; CTTGGACGGCGCTTGAGGAACC (SEQ ID NO:35)

3'RACE-1; GCCTACAAGCCAGTGGGATAG (SEQ ID NO:36)

cDNA-1; GCCAAGGACTATCTCTTGAGC (SEQ ID NO:37)

SKB-4;GGATGGACTCGAGCACTGGG (SEQ ID NO:38)

SKE2.2–4; AGAGGAGAGTGCAGACACTTTG (SEQ ID NO:39)

cDNA-3; GAGGACCCTGACGAGATCCCAAC (SEQ ID NO:40)

cDNA-9; CCATGTGTTCCCGTAGAGTCATTCC (SEQ ID NO:41)

2.2+SKE-1; ATGGAGCTCCAAGAAGGTGACATG (SEQ ID NO:42)

cDNA-5; CAGAAGTGTGGAGGGAAAGCGTCTGGC (SEQ ID NO:43)

cDNA-4; CCCTCAGACTGTTACACTCAGAAC (SEQ ID NO:44)

cDNA-2; CCCGTTGAGCGGAAAACTTCCTCT-CATGGC (SEQ ID NO:45)

cDNA-7; GGAAAGGATTCGTATGTGTCCGTGG (SEQ ID NO:46)

SKEN-5; GCAATGCGTTTGCTTTCTTCCAGTCATCT (SEQ ID NO:47)

cDNA-6; GAGGAGAGCAGAGAAGCAAT-GCGTTTGC (SEQ ID NO:48)

cDNA-8; GTTAGAGAGAAAATAAATAACCC (SEQ ID NO:49)

2.2+SKE-3; CCGTAAACAACACCGGATACAC (SEQ ID NO:50)

The amplification conditions are typically as follows. Reaction components: 10 mM Tris-HCl, pH 8.3, 50 mM potassium chloride, 1.5 mM magnesium chloride, 0.001% gelatin, 200 µM dATP, 200 µM dCTP, 200 µM dGTP, 200 µM dTTP, 0.4 µM primers, and 100 units per ml Taq polymerase. Program: 96 C for 3 min., 30 cycles of 96 C for 45 sec., 50 C for 60 sec., 72 for 60 sec, followed by 72 C for 5 min.

Standard nucleic acid hybridization techniques using the conditions disclosed above can then be used to identify full-length CDNA or genomic clones.

Control of ATR activity or Gene Expression

Since ATR genes are involved in controlling seed, in particular endosperm, development, inhibition of endogenous ATR activity or gene expression is useful in a number of contexts. For instance, reduction of ATR activity can be used for production of seed with enhanced endosperm. By reducing and/or eliminating ATR activity, plants with seed containing increased endosperm can be produced.

Alternatively, substantial inhibition of ATR activity can be used for production of fruit with small and/or degraded seed (referred to here as "seedless fruit") after fertilization. In many plants, particularly dicots, the endosperm is not persistent and eventually is degraded. Thus, in plants of the invention in which ATR activity is inhibited, embryo-less seed do not persist and seedless fruit are produced. For production of dicots with enhanced endosperm, the most beneficial effect may be to reduce, but not eliminate ATR activity. On the other hand, in monocots, which have persistent endosperm, it is advantageous to eliminate ATR activity.

Alternatively, plants of the invention can be used to prevent pre-harvest sprouting in seeds, especially those derived from cereals. In these plants, the endosperm persists and is the major component of the mature seed. Premature growth of embryos in stored grain causes release of degradative enzymes which digest starch and other components of the endosperm. Plants of the present invention are useful in addressing this problem because the seeds lack an embryo and thus will not germinate.

One of skill will recognize that a number of methods can be used to modulate ATR activity or gene expression. ATR activity can be modulated in the plant cell at the gene, transcriptional, posttranscriptional, translational, or posttranslational, levels. Techniques for modulating ATR activity at each of these levels are generally well known to one of skill and are discussed briefly below.

Methods for introducing genetic mutations into plant genes are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, for example, X-rays or gamma rays can be used.

Alternatively, homologous recombination can be used to induce targeted gene disruptions by specifically deleting or altering the ATR gene in vivo (see, generally, Grewal and Klar, *Genetics* 146: 1221–1238 (1997) and Xu et al., *Genes Dev.* 10:2411–2422 (1996)). Homologous recombination has been demonstrated in plants (Puchta et al., *Experientia* 50:277–284 (1994), Swoboda et al., *EMBO J.* 13:484–489 (1994); Offringa et al., *Proc. Natl. Acad. Sci. USA* 90: 7346–7350 (1993); and Kempin et al. *Nature* 389:802–803 (1997)).

In applying homologous recombination technology to the genes of the invention, mutations in selected portions of an ATR gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al. *Proc. Natl. Acad. Sci. USA* 91:4303–4307 (1994); and Vaulont et al. *Transgenic Res.* 4:247–255 (1995) are conveniently used to increase the efficiency of selecting for altered ATR gene expression in transgenic plants. The mutated gene will interact with the target wild-type gene in such a way that homologous recombination and targeted replacement of the wild-type gene will occur in transgenic plant cells, resulting in suppression of ATR activity.

Alternatively, oligonucleotides composed of a contiguous stretch of RNA and DNA residues in a duplex conformation with double hairpin caps on the ends can be used. The RNA/DNA sequence is designed to align with the sequence of the target ATR gene and to contain the desired nucleotide change. Introduction of the chimeric oligonucleotide on an extrachromosomal T-DNA plasmid results in efficient and specific ATR gene conversion directed by chimeric molecules in a small number of transformed plant cells. This method is described in Cole-Strauss et al. *Science* 273:1386–1389 (1996) and Yoon et al. *Proc. Natl. Acad. Sci. USA* 93:2071–2076 (1996).

Gene expression can be inactivated using recombinant DNA techniques by transforming plant cells with constructs comprising transposons or T-DNA sequences. ATR mutants prepared by these methods are identified according to standard techniques. For instance, mutants can be detected by PCR or by detecting the presence or absence of ATR mRNA, e.g., by Northern blots. Mutants can also be selected by assaying for development of endosperm in the absence of fertilization.

The isolated nucleic acid sequences prepared as described herein, can also be used in a number of techniques to control endogenous ATR gene expression at various levels. Subsequences from the sequences disclosed here can be used to control, transcription, RNA accumulation, translation, and the like.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque *Plant Sci.* (Limerick) 105:125–149 (1995); Pantopoulos In Progress in Nucleic Acid Research and Molecular Biology, Vol. 48. Cohn, W. E. and K. Moldave (Ed.). Academic Press, Inc.: San Diego, Calif., USA; London, England, UK. p. 181–238; Heiser et al. *Plant Sci.* (Shannon) 127:61–69 (1997)) and by preventing the accumulation of mRNA which encodes the protein of interest, (see, Baulcombe *Plant Mol. Bio.* 32:79–88 (1996); Prins and Goldbach *Arch. Virol.* 141:2259–2276 (1996); Metzlaff et al. *Cell* 88:845–854 (1997), Sheehy et al., *Proc. Nat. Acad. Sci. USA*, 85:8805–8809 (1988), and Hiatt et al., U.S. Pat. No. 4,801,340).

The nucleic acid segment to be introduced generally will be substantially identical to at least a portion of the endogenous ATR gene or genes to be repressed. The sequence, however, need not be perfectly identical to inhibit expression. The vectors of the present invention can be designed such that the inhibitory effect applies to other genes within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 7000 nucleotides is especially preferred.

A number of gene regions can be targeted to suppress ATR gene expression. The targets can include, for instance, the coding regions, introns, sequences from exon/intron junctions, 5' or 3' untranslated regions, and the like. In some embodiments, the constructs can be designed to eliminate the ability of regulatory proteins to bind to ATR gene sequences that are required for its cell- and/or tissue-specific expression. Such transcriptional regulatory sequences can be located either 5'-, 3'-, or within the coding region of the gene and can be either promote (positive regulatory element) or repress (negative regulatory element) gene transcription. These sequences can be identified using standard deletion analysis, well known to those of skill in the art. Once the sequences are identified, an antisense construct targeting these sequences is introduced into plants to control gene transcription in particular tissue, for instance, in developing ovules and/or seed. In one embodiment, transgenic plants are selected for ATR activity that is reduced but not eliminated.

Oligonucleotide-based triple-helix formation can be used to disrupt ATR gene expression. Triplex DNA can inhibit DNA transcription and replication, generate site-specific mutations, cleave DNA, and induce homologous recombination (see, e.g., Havre and Glazer *J. Virology* 67:7324–7331 (1993); Scanlon et al. *FASEB J*. 9:1288–1296 (1995); Giovannangeli et al. *Biochemistry* 35:10539–10548 (1996); Chan and Glazer *J. Mol. Medicine* (Berlin) 75:267–282 (1997)). Triple helix DNAs can be used to target the same sequences identified for antisense regulation.

Catalytic RNA molecules or ribozymes can also be used to inhibit expression of ATR genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Zhao and Pick *Nature* 365:448–451 (1993); Eastham and Ahlering *J. Urology* 156:1186–1188 (1996); Sokol and Murray *Transgenic Res*. 5:363–371 (1996); Sun et al. *Mol. Biotechnology* 7:241–251 (1997); and Haseloff et al. *Nature*, 334:585–591 (1988).

Another method of suppression is sense cosuppression. Introduction of nucleic acid configured in the sense orientation has been recently shown to be an effective means by which to block the transcription of target genes. For an example of the use of this method to modulate expression of endogenous genes (see, Assaad et al. *Plant Mol. Bio*. 22:1067–1085 (1993); Flavell *Proc. Natl. Acad. Sci. USA* 91:3490–3496 (1994); Stam et al. *Annals Bot*. 79:3–12 (1997); Napoli et al., *The Plant Cell* 2:279–289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed MRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using cosuppression technologies.

In a preferred embodiment, expression of a nucleic acid of interest can be suppressed by the simultaneous expression of both sense and antisense constructs (Waterhouse et al., *Proc. Natl. Acad. Sci. USA* 95:13959–13964 (1998). See also Tabara et al. *Science* 282:430–431 (1998).

Alternatively, ATR activity may be modulated by eliminating the proteins that are required for ATR cell-specific gene expression. Thus, expression of regulatory proteins and/or the sequences that control ATR gene expression can be modulated using the methods described here.

Another method is use of engineered tRNA suppression of ATR MRNA translation. This method involves the use of suppressor tRNAs to transactivate target genes containing premature stop codons (see, Betzner et al. *Plant J*. 11:587–595 (1997); and Choisne et al. *Plant J*. 11:597–604 (1997). A plant line containing a constitutively expressed ATR gene that contains an amber stop codon is first created. Multiple lines of plants, each containing tRNA suppressor gene constructs under the direction of cell-type specific promoters are also generated. The tRNA gene construct is then crossed into the ATR line to activate ATR activity in a targeted manner. These tRNA suppressor lines could also be used to target the expression of any type of gene to the same cell or tissue types.

ATR proteins may form homogeneous or heterologous complexes in vivo. Thus, production of dominant-negative forms of ATR polypeptides that are defective in their abilities to bind to other proteins in the complex is a convenient means to inhibit endogenous ATR activity. This approach involves transformation of plants with constructs encoding mutant ATR polypeptides that form defective complexes and thereby prevent the complex from forming properly. The mutant polypeptide may vary from the naturally occurring sequence at the primary structure level by amino acid substitutions, additions, deletions, and the like. These modifications can be used in a number of combinations to produce the final modified protein chain. Use of dominant negative mutants to inactivate target genes is described in Mizukami et al. *Plant Cell* 8:831–845 (1996).

Another strategy to affect the ability of an ATR protein to interact with itself or with other proteins involves the use of antibodies specific to ATR. In this method cell-specific expression of ATR-specific Abs is used inactivate fimctional domains through antibody:antigen recognition (see, Hupp et al. *Cell* 83:237–245 (1995)).

After plants with reduced ATR activity are identified, a recombinant construct capable of expressing low levels of ATR in embryos can be introduced using the methods discussed below. In this fashion, the level of ATR activity can be regulated to produce preferred plant phenotypes. For example, a relatively weak promoter such as the ubiquitin promoter (see, e.g., Garbarino et al. *Plant Physiol.* 109(4):1371–8 (1995); Christensen et al *Transgenic Res.* 5(3):213–8 (1996); and Holtorf et al. *Plant. Mol. Biol.* 29(4):637–46 (1995)) is useful to produce plants with reduced levels of ATR activity or expression. Such plants are useful for producing, for instance, plants that produce seed with enhanced endosperm.

Use of Nucleic Acids of the Invention to Enhance ATR Gene Expression

Isolated sequences prepared as described herein can also be used to introduce expression of a particular ATR nucleic acid to enhance or increase endogenous gene expression. For instance, without being bound to any theory, in light of ATR's relation to Exonuclease III, applicants believe that ATR binds DNA or chromatin and acts to modulate transcription. Enhanced expression can therefore be used to control plant morphology by controlling expression of genes under ATR's control in desired tissues or cells. Enhanced expression can also be used, for instance, to increase vegetative growth by preventing the plant from setting seed. Where overexpression of a gene is desired, the desired gene from a different species may be used to decrease potential sense suppression effects.

One of skill will recognize that the polypeptides encoded by the genes of the invention, like other proteins, have different domains that perform different functions. Thus, the gene sequences need not be full length, so long as the desired finctional domain of the protein is expressed.

Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

Preparation of Recombinant Vectors

To use isolated sequences in the above techniques, recombinant DNA vectors suitable for transformation of plant cells are prepared. Techniques for transforming a wide variety of flowering plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of Agrobacterium tumafaciens, and other transcription initiation regions from various plant genes known to those of skill. Such genes include for example, ACT11 from Arabidopsis (Huang et al. *Plant Mol. Biol.* 33:125–139 (1996)), Cat3 from Arabidopsis (GenBank No. U43147, Zhong et al., *Mol. Gen. Genet.* 251:196–203 (1996)), the gene encoding stearoyl-acyl carrier protein desaturase from *Brassica napus* (Genbank No. X74782, Solocombe et al. *Plant Physiol.* 104:1167–1176 (1994)), GPc1 from maize (GenBank No. X15596, Martinez et al. *J. Mol. Biol* 208:551–565 (1989)), and Gpc2 from maize (GenBank No. U45855, Manjunath et al., *Plant Mol. Biol.* 33:97–112 (1997)).

Alternatively, the plant promoter may direct expression of the ATR nucleic acid in a specific tissue or may be otherwise under more precise environmental or developmental control. Examples of environmental conditions that may effect transcription by inducible promoters include anaerobic conditions, elevated temperature, or the presence of light. Such promoters are referred to here as "inducible" or "tissue-specific" promoters. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Examples of promoters under developmental control include promoters that initiate transcription only (or primarily only) in certain tissues, such as fruit, seeds, or flowers. Promoters that direct expression of nucleic acids in ovules, flowers or seeds are particularly useful in the present invention. As used herein a seed-specific promoter is one which directs expression in seed tissues, such promoters may be, for example, ovule-specific (which includes promoters which direct expression in maternal tissues or the female gametophyte, such as egg cells or the central cell), embryo-specific, endosperm-specific, integument-specific, seed coat-specific, or some combination thereof. Examples include a promoter from the ovule-specific BEL1 gene described in Reiser et al. *Cell* 83:735–742 (1995) (GenBank No. U39944). Other suitable seed specific promoters are derived from the following genes: MAC1 from maize (Sheridan et al. *Genetics* 142:1009–1020 (1996), Cat3 from maize (GenBank No. L05934, Abler et al. *Plant Mol. Biol.* 22:10131–1038 (1993), the gene encoding oleosin 18 kD from maize (GenBank No. J05212, Lee et al. *Plant Mol. Biol.* 26:1981–1987 (1994)), vivparous-1 from Arabidopsis (Genbank No. U93215), the gene encoding oleosin from Arabidopsis (Genbank No. Z17657), Atmyc1 from Arabidopsis (Urao et al. *Plant Mol. Biol.* 32:571–576 (1996), the 2s seed storage protein gene family from Arabidopsis (Conceicao et al. *Plant* 5:493–505 (1994)) the gene encoding oleosin 20 kD from *Brassica napus* (GenBank No. M63985), napA from Brassica napus (GenBank No. J02798, Josefsson et al. *JBL* 26:12196–1301 (1987), the napin gene family from *Brassica napus* (Sjodahl et al. *Planta* 197:264–271 (1995), the gene encoding the 2S storage protein from *Brassica napus* (Dasgupta et al. *Gene* 133:301–302 (1993)), the genes encoding oleosin A (Genbank No. U09118) and oleosin B (Genbank No. U09119) from soybean and the gene encoding low molecular weight sulphur rich protein from soybean (Choi et al. *Mol Gen, Genet.* 246:266–268 (1995)).

In addition, the promoter sequences from the ATR genes disclosed here can be used to drive expression of the ATR polynucleotides of the invention or heterologous sequences. The sequences of the promoters are identified below.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. Nature 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and *Binding, Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. ofPlant Phys.* 38:467–486 (1987).

The nucleic acids of the invention can be used to confer desired traits on essentially any plant. Thus, the invention has use over a broad range of plants, including species from the genera Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna, and Zea.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Seed obtained from plants of the present invention can be analyzed according to well known procedures to identify plants with the desired trait. If antisense or other techniques are used to control ATR gene expression, Northern blot analysis can be used to screen for desired plants. In addition, the presence of fertilization independent reproductive development can be detected. Plants can be screened, for instance, for the ability to form embryo-less seed, form seed that abort after fertilization, or set fruit in the absence of fertilization. These procedures will depend, part on the particular plant species being used, but will be carried out according to methods well known to those of skill.

The following Examples are offered by way of illustration, not limitation.

EXAMPLE

The following example is offered to illustrate, but no to limit the claimed invention.

Example 1

This example shows the characterization of atr mutant plants and the isolation of ATR.

Arabidopsis plants were transformed by infiltrating them with Agrobacterium containing the SKI15 T-DNA vector (generously provided by D. Weigel (Salk Institute, La Jolla, Calif.)). T1 seeds were harvested. The SKI15 vector has the bialaphos resistance (BAR) gene that allowed us to directly select transgenic plants in soil after spraying with the commercially available herbicide, Basta. Siliques from approximately 5,000 Basta resistant plants were opened, and those displaying approximately 50% seed abortion were identified.

Two lines, B13 and B33, were identified for firther characterization. Genetic analysis of the mutants revealed that the atr mutants were female sterile. Male fertility, however, depended on the genetic background of the mutant alleles. For instance, in the Columbia background, transmission of the atr mutation is less than 50%. However, in the Landsberg erecta background, transmission through the male was almost normal.

Molecular analysis confirmed that the two mutations were allelic. For example, both the B13 and B33 alleles carry the SKI15 T-DNA within an ATR exon, confirming that disruption of the ATR gene resulted in the observed B13 and B33 phenotypes.

5'- and 3'-RACE were used to delineate the 5'- and 3'-ends of the cDNA, respectively. 5'-RACE was carried out using reagents and protocols provided by 5' RACE System for Rapid Amplification of cDNA Ends, Version 2.0, GIBCO BRL, LIFE TECHNOLOGIES, Grand Island, N.Y. and Marathon cDNA Amplification Kit, Clontech, Palo Alto, Calif. Final gene specific 5'-RACE primers were SKES-4 (GGGAACAAGTGCACCATCTCC; SEQ ID NO:29) and SKES3.5 (CGATGATACTGTCTCTTCGAGC; SEQ ID NO:25). 3'-RACE was carried out using reagents and protocols provided by Marathon cDNA Amplification Kit, Clontech, Palo Alto. Final gene-specific 3' end was obtained from cDNA library screening.

The nucleotide sequence of the genomic copy of ATR1 was also determined (SEQ ID NO:1). The 5'-end of the ATR RNA is located at position 3,425 of SEQ ID NO:1. The position of the 3'-end of the ATR RNA is at position 12,504 of SEQ ID NO:1. The position of the ATG translation initiation codon is at position 4,903 of SEQ ID NO:1. The position of the TAA translation termination codon is at position 12,321 of SEQ ID NO:1.

A portion of the ATR polynucleotide sequence, including the first exon, is encompassed by the bacterial artificial chromosome (BAC) clone T9J15TRB. For example, sequences 3820–4299, 4319–4558, 4546–5025 and 9320–9777 of SEQ ID NO:1 were previously determined using the BAC clone as a template. Moreover, a separate independently sequenced region (Bork, C. et al *Gene* 28:147–153 (1998)) also overlaps the ATR sequence at positions 11,087 to 12,785 of SEQ ID NO:1.

The predicted ATR protein has 1,729 amino acids. This sequence was compared to known protein sequences using BLAST and revealed homology to several Endonuclease III proteins. The highest homology was to the Endonuclease III protein from *Deinococcus radiodurans*, Genbank Accession No. AE002073 (see, e.g., White, O. et al. *Science* 286:1571–1577 (1999)). Other ATR motifs include two consecutive nuclear localization signals at positions 43–60 and 61–78 and a leucine zipper at positions 1330–1351.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated nucleic acid compirsing a polynucleotide sequence, or complement thereof, encoding an ATR polypeptide exhibiting at least 80% sequence identity to SEQ ID NO:2, wherein the nucleic acid, when introduced into a plant to inhibit expression, results in a plant with increased endosperm development and wherein the ATR polypeptide comprises a leucine zipper and a nuclear localization signal sequence.

2. The isolated nucleic acid of claim 1, wherein the ATR polypeptide comprises SEQ ID NO:2.

3. The isolated nucleic acid of claim 1, wherein the polynucleotide sequence comprises SEQ ID NO:5.

4. The isolated nucleic acid of claim 1, wherein the polynucleotide sequence comprises SEQ ID NO:1.

5. The isolated nucleic acid of claim 1, wherein the nucleic acid further comprises a promoter operably linked to the polynucotide sequence.

6. The isolated nucleic acid of claim 5, wherein the promoter is a constitutive promoter.

7. The isolated nucleic acid of claim 5, wherein the polynucleotide sequence is linked to the promoter in an antisense orientation.

8. A method of introducing an isolated nucleic acid into a host cell comprising:

(a) providing an isolated nucleic acid according to claim 1; and (b) contacting the nucleic acid with the host cell under conditions that permit insertion of the nucleic acid into the host cell.

9. The isolated nucleic acid of claim 1, wherein the polypeptide exhibits at least 90% sequence identity to SEQ ID NO:2.

10. An expression cassette comprising a promoter operably linked to a heterologous polynucleotide sequence, or a complement thereof, encoding an ATR polypeptide exhibiting at least 80% sequence identity to SEQ ID NO:2, wherein the nucleic acid, when introduced into a plant to inhibit expression, results in a plant with increased endosperm development and wherein the ATR polypeptide comprises a leucine zipper and a nuclear localization signal sequence.

11. The expression cassette of claim 10, wherein the ATR polypeptide comprises SEQ ID NO:2.

12. The expression cassette of claim 11, wherein the polynucleotide sequence comprises SEQ ID NO:5.

13. The expression cassette of claim 10, wherein the polynucleotide sequence comprises SEQ ID NO:1.

14. The expression cassette of claim 10, wherein the promoter is a constituive promoter.

15. The expression cassette of claim 10, wherein the polynucleotide sequence is linked to the promoter in an antisense orientation.

16. A host cell comprising an exogenous nucleic acid comprising a polynucleotide sequence, or complement thereof, encoding an ATR polypeptide exhibiting at least 80% sequence identity to SEQ ID NO:2, wherein the nucleic acid, when introduced into a plant to inhibit expression, results in a plant with increased endosperm development and wherein the ATR polypeptide comprises a leucine zipper and a nuclear localization signal sequence.

17. The host cell of claim 16, wherein the nucleic acid firther comprises a promoter operably linked to the polynucleotide sequence.

18. The host cell of claim 17, wherein the promoter is operably linked to the polynucleotide sequence in an antisense orientation.

19. The host cell of claim 17, wherein the promoter is constitutive.

20. A method of modulating transition of an ATR polynucleotide, the method comprising, introducing into a host cell an expression cassette comprising a promoter operably linked to an ATR polynucleotide, or complement thereof, encoding an ATR polypeptide at least 80% identical to SEQ ID NO:2, wherein the ATR polypeptide comprises a leucine zipper and a nuclear localization signal sequence; and detecting a host cell with modulated transciption of a polynucleotide encoding an ATR polypeptide at least 80% identical to SEQ ID NO:2 compared to a host cell wherein the expression cassette is not introduced.

21. The method of claim 20, wherein the ATR polynucleotide encodes SEQ ID NO:2.

22. The method of claim 20, wherein the ATR polynucleotide comprises SEQ ID NO:5.

23. The method of claim 20, wherein the ATR polynucleotide comprises SEQ ID NO:1.

24. The method of claim 20, wherein the expression cassette is introduced by Agrobacterium.

25. The method of claim 20, wherein the expression cassette is introduced by a sexual cross.

26. The method of claim 20, wherein modulating transcription results in the modulation of endosperm development in a plant.

27. The method of claim 26, wherein endosperm development is enhanced.

28. The method of claim 26, wherein endosperm development is decreased.

29. The method of claim 20, wherein the ATR polynucleotide encodes SEQ ID NO:2 and the promoter is operably linked to the ATR polynucleotide in the antisense orientation.

30. The method of claim 20, wherein the host cell is a plant cell.

31. A transgenic plant cell or transgenic plant comprising a heterologous nucleic acid comprising a polynucleotide sequence, or complement thereof, encoding an ATR polypeptide exhibiting at least 80% sequence identity to SEQ ID NO:2, wherein the nucleic acid, when introduced into a plant to inhibit expression, results in a plant with increased endosperm development and wherein the ATR polypeptide comprises a leucine zipper and a nuclear localization signal sequence.

32. The transgenic plant cell or transgenic plant of claim 31, wherein the ATR polypeptide comprises SEQ ID NO:2.

33. The transgenic plant cell or transgenic plant of claim 32, wherein the polynucleotide sequence comprises SEQ ID NO:5.

34. The transgenic plant cell or transgenic plant of claim 31, wherein the polynucleotide sequence comprises SEQ ID NO:1.

35. The transgenic plant cell or transgenic plant of claim 31, wherein the nucleic acid further comprises a promoter operably linked to the polynucleotide sequence.

36. The transgenic plant cell or transgenic plant of claim 35, wherein the promoter is a constitutive promoter.

37. The transgenic plant cell or transgenic plant of claim 31, wherein the polynucleotide sequence is linked to the promoter in an antisense orientation.

38. A plant which has been regenerated from a plant cell according to 31.

* * * * *

UNITED STATES PATENT AND TRADEMARK OFFICE
CERTIFICATE OF CORRECTION

PATENT NO.        : 6,476,296 B1                                   Page 1 of 1
APPLICATION NO.   : 09/553690
DATED             : November 5, 2002
INVENTOR(S)       : Robert L. Fischer et al.

It is certified that error appears in the above-identified patent and that said Letters Patent is hereby corrected as shown below:

In claim 20, column 73, line 55:

kindly change "transiption" to --transcription--

In claim 38, column 74, line 58:

kindly change "to 31" to --to claim 31--

Signed and Sealed this

Thirtieth Day of January, 2007

JON W. DUDAS
*Director of the United States Patent and Trademark Office*

SEQUENCE LISTING

```
<160> NUMBER OF SEQ ID NOS:  50

<210> SEQ ID NO 1
<211> LENGTH: 12785
<212> TYPE: DNA
<213> ORGANISM: Arabidopsis sp.
<220> FEATURE:
<223> OTHER INFORMATION: ATROPOS (ATR) genomic sequence

<400> SEQUENCE: 1
aagcttaaag ctaccaacat cgaatttagt aaaagaccca tgatttgaaa ttggaattgt      60
cggcaaaatc gagaagatat agagccgaca cgggaacagt gaaaaccaca aagcgcgtaa     120
gaatgaaaca gtgggagaag gaagagagaa tcttaccgat cattcgaggg aaaagatggg     180
aatcagagaa aaatctggaa aaaaagaaat taagagaaag agagagaaga aagtgaggag     240
gaagatgcag tgaagactgc tatagccaca tcccacatgg tgtgatgaga gagagagaga     300
gagaggttaa agcagcaaat tgtggagaga taaagagaga gagagactga gcgagtcaag     360
ttcgtcgtcg tgtttaaaag aaagaatcct atatttgcct ttttctttac tactttattt     420
tcagactatt tgcttatttt gcctcaaact tttttgattg tcacttttcg atcctaaagt     480
gtttgacaat ttacctgcct ttttctccaa gaaaaatcag aacagaccac agcaaattta     540
tgtattttct attaaaaaag aaagaaagaa ttcatattac ttatagaatt aaaagctaag     600
cagttgaaaa cgtgaaagca gaatttctaa aaaaaatagt aaactgctac aaacttattt     660
atgtgtatat aacatatcta taaagaaact caaatatatg ataaatcatt ttaacaaaat     720
ttctatgaaa ttataataaa aaaagtcact tttgacactt aaaaggttga caataaccgt     780
ctctccaaaa aaaaatcaaa acatttataa tttctaaaac tatggtgtaa ttttgctgaa     840
atcaaaaaga aagaaggat ttctatatca taagtttcat tattgtatca aactttcaaa     900
tttcatgtaa tttgaaagga aaaaattaa gatataatgt tgttttttgtt tcttatgtta     960 cattttcatg gaatatatat tcataacaaa aaatgtattt taatatgatg agagattacc    1020
atccaaaagg tcgaacttat ataaacaag ttaataacta aacaatacat gtgatcacaa     1080
```

```
tcaatgacag ttttgatctt aaaatagaaa tgattgagca aacctcaaaa atgtcttctt    1140
aggatcacaa aatctttcct ttagcttatt aaagccggga gttcaactct ctctcccttg    1200
tagacttttt gttttcaaat ctttttcttt caaaaaatca ataattagtt aatgggcata    1260
atatttggtt ttaattaagt ccatagattt tttaggacca tctctaatca cgacaaatat    1320
cctaaattgt aacacattta aaacttaaaa gtattgcatt cacaatcctt aaaatatata    1380
tatatatata tatatatata tatatatata tatatgaaag ttatatagaa acgataactc    1440
cttactcaac aattagccca aaaaaacatc cataatgcat ttaaactagg aattttaaca    1500
aactcaaata ggttggtagt taaaaaaaaa caaatagtag atgtacatac gtacctttaa    1560
aaatatatac tcatatcgaa agtttttaaat tttgcgaaat taaatacatt tatctatcaa    1620
ttaaaataca tttaataatg cataattctg taatatctat ctttaatttc catatagaac    1680
caaaacaaaa taaacatatc aaatagtttt aacttaacaa aaacgttagg gaaaagttga    1740
cctaactagc ttgattgacg ttgaacttgt caatgcgaaa gcgatatttc caatatatac    1800
tacatgtagt attatttata tggaagtttc taaaaaggtg ttgagtggat tgttacttgt    1860
tggaggatgc tattttttcc ttcttgccat aatattttac gagtatggga taactacata    1920
ctcatgatta tgaaacgctc actttatttg aaaaacctcc taatacacca aatatgtcac    1980
tagattccaa aacgtagacc aattgtatct aatctcaaat tctcaatcaa agtattaatt    2040
taccgatggt aagaaaagtt aaccgatata attatcaaaa gaaagaataa gtcaacagat    2100
tcttaatctc tttattttgg tatatgaaca tttgtacaaa aatctcaaaa gatatgtaac    2160
tgtttaaaat ataaattcac tgagattaat tcttcagact cgtgttagct ataataatgt    2220
caagagttct tcttgtttca aggaaaaacc ttaaagatat gtatattttc tgtaattatg    2280
atgatataat ttgctattca ttgtcacaaa cattactttta aaaatcgta ttttcattac    2340 tacaatgttg actaagaaca aaaatacatt gattattgat atatcgtcaa ctgaattttc    2400
ttccgaggga tataattctc aaacatagca agaatctcat aataatgttt cgtgactacc    2460
tttagacgaa attttttttaa gattcgtaac gtgacttatg gtctcttgct gtggggtca    2520 atgcgaataa atctaaatgt atgggagtca aataaaatac caagaaaaat aaaggagcag    2580
cacccaataa actatatggg accagaaatc ctttcattgg tttaaaatag gattatcccg    2640
aaagatgaag gactaaattg aaactgattg ggggtaggaa gagatccgtc acaatcatta    2700
atggcttcca cgcggaaact tgtcgtttat acaatttcat taactttcgg gtcgggttta    2760
tattccaaat gggtcaaata atattagttt aatacactaa cggagtaatt aattggtgac    2820 tacaattttta tcagtttggt gcaattagaa acgaacatag tcgtaaaata cgagttcggt    2880
gttatacctt tatttacgtt aaaaaaatac gagaattttg tgtcaaattt caaattaatt    2940
tcatgaatat atggaaatta ttagatactc tagcgaaaat agtgattatg agcgttttac    3000
aaaaatacga ttttagcatt gaacttcctt tatgtaattc ggtcaaatgt tggcatgaag    3060
aagcaagttt gcaacattaa atttcattta aaaatcgtgt tgacatactt taaaatctaa    3120 ataggaag aagaccaaaa cattaaattt agtaagattc taatgaacat ttataagtta    3180
taacttataa ccaacaaaag ttgggtttag cgttgttgct ttatctgaaa acttgcaaac    3240
taaccatttt taataggact aatgacaatt aacaacaaaa tacacttaag caacaacgtc    3300
ctcgtgaata taatttgggc ctcaggccca tattgctaac gccaactgat atttcacttt    3360
attccttctt catctcacca cactctctct ctatctctat ctctaacggc atagctgact    3420
cagtgttctc cggcattgac tcgcctgaga atcagaaagc ttagatcggt gagcttttag    3480
```

```
ctccattttc tgtttattta catattattt ccttttttc tctctccctt ttttatctgg    3540
aatttgttct gctaaatttt ccagctgtta cattttccga tcacgagaag aatcactggg    3600
tttttatgtt aatcaataca tgttcctgtt ttctgatcat aaatctcagc tattaacacc    3660
tgattttgat tctgcgtaat aaaaacctct gatttgcttt tatcttcact ttccccataa    3720
acattgctta ctttattcgc tcttctttta ccgtttccag ctaaaaaatt cttcgctatt    3780
caatgtgttt ctcgttttgt tgatgagaaa aatatctgac aaaaaatcat ttattgcatt    3840
ttatggtgca gattcttagt taatgtcgcc ttctctaacc aagtcagatt aaaaaggagt    3900
gttcgtccat gttgctttgt tttggtgttt ggagagagtt ttcggagagt taggtgagtg    3960
ttatttgggg tgaggtagtg ataaggtttg aaggggagt gattcatcaa gtgtgttatg    4020
aattcgaggg ctgatccggg ggatagatat tttcgagttc ctttggagaa tcaaactcaa    4080
caagagttca tgggttcttg gattccattt acacccaaaa aacctagatc aagtctgatg    4140
gtagatgaga gagtgataaa ccaggatcta aatgggtttc caggtggtga atttgtagac    4200
agggattct gcaacactgg tgtggatcat aatgggtttt tgatcatgg tgctcatcag    4260
ggcgttacca acttaagtat gatgatcaat agcttagcgg gatcacatgc acaagcttgg    4320
agtaatagtg agagagatct tttgggcagg agtgaggtga cttctccttt agcaccagtt    4380
atcagaaaca ccaccggtaa tgtagagccg gtcaatggaa atttttacttc agatgtgggt    4440
atggtaaatg gtccttttcac ccagagtggc acttctcaag ctggctataa tgagtttgaa    4500
ttggatgact tgttgaatcc tgatcagatg ccctttctcct tcacaagctt gctgagtggt    4560
ggggatagct tattcaaggt tcgtcaatgt gagtgatcaa atctatttc agttttttt    4620
tttccctttc ttccgttctt gcagtactta gagtagaaca tgaattagaa tatcttaaga    4680
aagtcatggt tttgaacaga tggacctcca gcgtgtaaca agcctcttta caatttgaat    4740
tcaccaatta gaagagaagc agttgggtca gtctgtgaaa gttcgtttca atatgtaccg    4800
tcaacgccca gtctgttcag aacaggtgaa aagactggat tccttgaaca gatagttaca    4860
actactggac atgaaatccc agagccgaaa tctgacaaaa gtatgcagag cattatggac    4920
tcgtctgctg ttaatgcgac ggaagctact gaacaaaatg atggcagcag acaagatgtt    4980
ctggagttcg accttaacaa aactcctcag cagaaaccct ccaaaaggaa aaggaagttc    5040
atgcccaagg tggtcgtgga aggcaaaacct aaagaaagc cacgcaaacc tgcagaactt    5100
cccaaagtgg tcgtggaagg caaacctaaa aggaagccac gcaaagctgc aactcaggaa    5160
aaagtgaaat ctaaagaaac cgggagtgcc aaaaagaaaa atttgaaaga atcagcaact    5220
aaaaagccag ccaatgttgg agatatgagc aacaaaagcc ctgaagtcac actcaaaagt    5280
tgcagaaaag ctttgaattt tgacttggag aatcctggag atgcgaggca aggtgactct    5340
gagtctgaaa ttgtccagaa cagtagtggc gcaaactcgt tttctgagat cagagatgcc    5400
attggtggaa ctaatggtag tttcctggat tcagtgtcac aaatagacaa gaccaatgga    5460
ttggggcta tgaaccagcc acttgaagtg tcaatggaa accagccaga taaactatct    5520
acaggagcga aactggccag agaccaacaa cctgatttat tgactagaaa ccagcaatgc    5580
cagttcccag tggcaaccca gaacacccag ttcccaatgg aaaaccaaca gcttggctt    5640
cagatgaaaa accaacttat tggctttcca tttggtaacc agcaacctcg catgaccata    5700
agaaaccagc agccttgctt ggccatgggt aatcaacaac ctatgtatct gataggaact    5760
ccacggcctg cattagtaag tggaaaccag caactaggag gtccccaagg aaacaagcgg    5820
```

-continued

```
cctatatttt tgaatcacca gacttgttta cctgctggaa atcagctata tggatcacct    5880
acagacatgc atcaacttgt tatgtcaacc ggagggcaac aacatggact actgataaaa    5940
aaccagcaac ctggatcatt aataagaggc cagcagcctt gcgtaccttt gattgaccag    6000
caacctgcaa ctccaaaagg ttttactcac ttgaatcaga tggtagctac cagcatgtca    6060
tcgcctgggc ttcgacctca ttctcagtca caagttccta caacatatct acatgtggaa    6120 tctgttttcca ggattttgaa tgggactaca ggtacatgcc agagaagcag ggctcctgca    6180
tacgattctt tacagcaaga tatccatcaa ggaaataagt acatactttc tcatgagata    6240
tccaatggta atgggtgcaa gaaagcgtta cctcaaaact cttctctgcc aactccaatt    6300
atggctaaac ttgaggaagc cagggggctcg aagagacagt atcatcgtgc aatgggacag    6360
acggaaaagc atgatctaaa cttagctcaa cagattgctc aatcacaaga tgtggagaga    6420
cataacagca gcacgtgtgt ggaatattta gatgctgcaa agaaaacgaa atccagaaa    6480 gtagtccaag aaaatttgca tggcatgcca cctgaggtta tagaaatcga ggatgatcca    6540
actgatgggg caagaaaagg taaaaatact gccagcatca gtaaaggtgc atctaaagga    6600
aactcgtctc cagttaaaaa gacagcagaa aaggagaaat gtattgtccc aaaaacgcct    6660
gcaaaaaagg gtcgagcagg tagaaaaaaa tcagtacctc cgcctgctca tgcctcagag    6720
atccagcttt ggcaacctac tcctccaaag acacctttat caagaagcaa gcctaaagga    6780
aaagggagaa agtccataca agattcagga aaagcaagag gtaactaatg tattctacaa    6840
tctctgtgat ataattttga gattttagta actgatgtgt ccaaaccagc tccttatcac    6900
tgttggtgcg ttgtataggt ccatcaggag aacttctgtg tcaggattct attgcggaaa    6960
taatttacag gatgcaaaat ctgtatctag gagacaaaga aagagaacaa gagcaaaatg    7020
caatggtctt gtacaaagga gatggtgcac ttgttcccta tgagagcaag aagcgaaaac    7080
caagacccaa agttgacatt gacgatgaaa caactcgcat atggaactta ctgatgggga    7140
aaggagatga aaagaaggg gatgaagaga aggataaaaa gaaagagaag tggtgggaag    7200
aagaaagaag agtcttccga ggaagggctg attccttcat cgctcgcatg cacctggtac    7260
aaggtgaaga tccacttctc ttctcaactc cattttttatt cacacaaatt agtagaatac    7320
tcaaaaatga tgttttgttt gcaaaatttt aaaattcact agttaaccat gtcaaataat    7380
attcataatg catcttgtga agaacaggtg tgcatttatg gtgacagctg aatggtttat    7440
gtgcctatta tttcttttac tgctatagat gaccaattga acttaaacgt ttacaggaga    7500
tagacgtttt tcgccatgga agggatcggt ggttgattcg gtcattggag ttttccttac    7560
acagaatgtc tcggatcacc tttcaaggta tatgagttgc cttaataaat tgagttccaa    7620
aacatagaaa ttaacccatg gtggttttac aatgcagctc tgcgttcatg tctctagctg    7680
ctcgattccc tccaaaatta agcagcagcc gagaagatga aaggaatgtt agaagcgtag    7740
ttgttgaaga tccagaagga tgcattctga acttaaatga aattccttcg tggcaggaaa    7800
aggttcaaca tccatctgac atggaagttt ctggggttga tagtggatca aaagagcagc    7860
taagggactg ttcaaactct ggaattgaaa gatttaattt cttagagaag agtattcaaa    7920
atttagaaga ggaagtatta tcatcacaag attcttttga tccggcgata tttcagtcgt    7980
gtgggagagt tggatcctgt tcatgttcca aatcagacgc agagtttcct acaaccaggt    8040
gtgaaacaaa aactgtcagt ggaacatcac aatcagtgca aactgggagc ccaaacttgt    8100
ctgatgaaat ttgtcttcaa gggaatgaga gaccgcatct atatgaagga tctggtgatg    8160
ttcagaaaca agaaactaca aatgtcgctc agaagaaacc tgatcttgaa aaacaatga    8220
```

```
attggaaaga ctctgtctgt tttggtcagc caagaaatga tactaattgg caaacaactc    8280
cttccagcag ctatgagcag tgtgcgactc gacagccaca tgtactagac atagaggatt    8340
ttggaatgca gggtgaaggc cttggttatt cttggatgtc catctcacca agagttgaca    8400
gagtaaagaa caaaaatgta ccacgcaggt ttttcagaca aggtggaagt gttccaagag    8460
aattcacagg tcagatcata ccatcaacgc ctcatgaatt accaggaatg ggattgtccg    8520
gttcctcaag cgccgtccaa gaacaccagg acgataccca acataatcaa caagatgaga    8580
tgaataaagc atcccattta caaaaaacat ttttggatct gctcaactcc tctgaagaat    8640
gccttacaag acagtccagt accaaacaga acatcacgga tggctgtcta ccgagagata    8700
gaactgctga agacgtggtt gatccgctca gtaacaattc aagcttacag aacatattgg    8760
tcgaatcaaa ttccagcaat aaagagcaga cggcagttga atacaaggag acaaatgcca    8820
ctattttacg agagatgaaa gggacgcttg ctgatgggaa aaagcctaca agccagtggg    8880
atagtctcag aaaagatgtg gaggggaatg aagggagaca ggaacgaaac aaaaacaata    8940
tggattccat agactatgaa gcaataagac gtgctagtat cagcgagatt tctgaggcta    9000
tcaaggaaag agggatgaat aacatgttgg ccgtacgaat taaggtaaat ctactaattt    9060
cagttgagac cctcatcaaa tctgtcagaa ggcttgaaca tcagtaaatt atgtaaccat    9120
atttacaaca ttgcaggatt cctagaacg gatagttaaa gatcatggtg gtatcgacct    9180
tgaatggttg agagaatctc ctcctgataa agccaagtgg gtaaatcaca tttttagtga    9240
ctgcaacact agcacgatcg atttactcaa caattacgtc aaactgagta ttaacaagtt    9300
gctcatgaac atttcacagg gactatctct gagcataag aggtctgggt ttgaaaagtg    9360
ttgaatgcgt gcgactctta acactccaca atcttgcttt ccctgtgagt cagactattc    9420
cattatctac taaaaactta gaataactcc ggctaactaa gctggaactt gtattgatga    9480
tatgaaggtt gacacgaatg ttggaaggat agcagttagg atgggatggg tgcctctaca    9540
accctacct gaatcacttc agttacacct cctggagctg taagtttctt tttgtttgtc    9600
atctaaacaa cgaaatttt atgcaagtca taaccatgct gtgttttcac agatacccag    9660
tgctcgagtc catccaaaaa tttctttggc caagactttg caaactcgat caacgaacac    9720
tgtatgctca taaactctaa caaatcatct gtctgaaaaa ccaatatttc tttggtagaa    9780
ttctattgtc attactcatt actaacagcg aaattaatta acgttctttt tcttactcag    9840
gtatgaatta cactaccaac tgattacgtt tggaaaggta ttattgctct aagctttgaa    9900
tttatcatat ggtaatttca agcattgtag gcacctgatc aattatgtgt ctaaatcatg    9960
tgaattcatg tcaggtattt tgcacaaaga gtagaccaaa ttgtaatgca tgtccaatga   10020
gaggagagtg cagacacttt gccagtgctt atgctaggta agcaagcttt catgtactta   10080
tatgcaataa ttaaagataa aatttaggat tatgggtaag ttacaaaaaa ttaggctcag   10140
tttcatggta gctagctgga aatagtatta caagaacaac ataaagatca aagacagaat   10200
catggatcca tatgcactat cattttagct cttgtaatcc atacatgaac actatatgcc   10260
aaagtaggga tttcaaatat gagattcgat gactgatgcc attgtaacag tgcaagactt   10320
gctttaccgg caccagagga gaggagctta acaagtgcaa ctattccggt ccctcccgag   10380
tcctatcctc ctgtagccat cccgatgata gaactacctc ttccgttgga gaaatcccta   10440
gcaagtggag caccatcgaa tagagaaaac tgtgaaccaa taattgaaga gccggcctcg   10500
cccgggcaag agtgcactga ataaccgag agtgatattg aagatgctta ctacaatgag   10560
```

-continued

```
gaccctgacg agatcccaac aataaaactc aacattgaac agtttggaat gactctacgg    10620
gaacacatgg aaagaaacat ggagctccaa gaaggtgaca tgtccaaggc tttggttgct    10680
ttgcatccaa caactacttc tattccaact cccaaactaa agaacattag ccgtctcagg    10740
acagagcacc aagtgtaagc taatatctcc tcctatattt tatcttccat ataaattttg    10800
gggaaaaaat cgctctccat ctggttttag aacatgcggg tcagccaggg ttatggcatt    10860
tttatatatt tcaccgatcg gcccgagctg gctctggttg actcgtatgc caccctgcat    10920
tgaacaaacc agtaggagac aagcaagcaa acgttttaa gataaggtct atggtaaaat    10980
gacaaggtaa ctgataaatg tgtcgtctat ttgcaggtac gagctcccag attcacatcg    11040
tctccttgat ggtgtaagtc aatttttaac tctctctata ctcgagttgt ttcacttgag    11100
caacactgtt taaaagtcct catttgataa aataacagat ggataaaaga gaaccagatg    11160
atccaagtcc ttatctctta gctatatgga caccaggtga aataaaaact gcaatgtttc    11220
attcatgtgt ctacagtatc aaagaaagta cagctagagc taaaaagcat ttgaaataga    11280
gtcggttaaa tatgaaagtt tgaatctgta aatgaaagcc ggaacgtagc attggtggat    11340
gttatatgta aattagtttt tgagattggt ctaatgtagt tgtttgactg ccaggtgaaa    11400
cagcgaattc ggcacaaccg cctgaacaga agtgtggagg gaaagcgtct ggcaaaatgt    11460
gctttgacga gacttgttct gagtgtaaca gtctgaggga agcaaactca cagacagttc    11520
gaggaactct tctggtgaga ttatcttgat cttttgtgtt gctcatgaaa aggagaagtg    11580
agaatacaag tttgctaata tcattttttc gtcattcaca gataccttgt cggactgcca    11640
tgagaggaag ttttccgctc aacgggacat atttccaagt caacgaggtt agatgaaata    11700
aaactcaaac agacagacga aacattattt ctgtttagtt ttggttcttt atcctccttg    11760 ccattttta tcttgcagtt atttgcagac cacgagtcca gtctcaaacc catcgatgtt    11820
cctagagatt ggatatggga tctcccaaga aggactgttt acttcggaac atcagtaaca    11880
tcaatattca gaggtaaaaa cattcgtaat agagttagtt aatcaaatgt ccaaaacaca    11940
agaaagcttc accgtccaat acacaagaaa gcttcacctt ctctttgcca aaaaagatct    12000
tagaatgttt tgctgaattt gtgcaggtct ttcaacggag cagatacagt tctgcttttg    12060
gaaaggtaaa cgttaacttt cgacccagag aaatccggaa aatctattgc tttgttctga    12120
tcaatacgtt aaacatatac acacacactt tacacttagg accaatactg ttctgatctg    12180
tgatagaaac tggtaaacat ctaacaatta tgattgcagg attcgtatgt gtccgtggat    12240
tcgaacagaa gacaagagca ccgcgtccat taatggcaag gttgcatttt cctgcgagca    12300
aattgaagaa caacaaaacc taaagatgac tggaagaaag caaacgcatt gcttctctgc    12360
tctcctctat ttaaagccag gaaaagtccc atttagacat aataacagga atccaaatag    12420
gctattttct ctttctttct tatttcattc atagagcaga agcgacacaa aaaagttttt    12480
tgggttattt attttctctc taacaaattt gtagcgtttt gggtcttttt ctggctgtca    12540
ctagcgtggc aaatccaatg tccgcgcaca cttaggcgca ttgtcaataa attctccggc    12600
caccggagtg ttacgatctt ttccaacggc ggctaatgcg atatttccgg taacacatat    12660
tccttattct atgttggttt tgtgtacggc gtgggcctta ctagacaatg atcatcaata    12720
aaactaacac aaagttgaat gctacaaagt agaaagtgaa gaaaaaataa tatagacatt    12780
gccga                                                                12785
```

<210> SEQ ID NO 2
<211> LENGTH: 1729

<212> TYPE: PRT
<213> ORGANISM: Arabidopsis sp.
<220> FEATURE:
<223> OTHER INFORMATION: ATROPOS (ATR) amino acid sequence

<400> SEQUENCE: 2

```
Met Gln Ser Ile Met Asp Ser Ser Ala Val Asn Ala Thr Glu Ala Thr
 1               5                  10                  15
Glu Gln Asn Asp Gly Ser Arg Gln Asp Val Leu Glu Phe Asp Leu Asn
                20                  25                  30
Lys Thr Pro Gln Gln Lys Pro Ser Lys Arg Lys Arg Lys Phe Met Pro
            35                  40                  45
Lys Val Val Glu Gly Lys Pro Lys Arg Lys Pro Arg Lys Pro Ala
        50                  55                  60
Glu Leu Pro Lys Val Val Glu Gly Lys Pro Lys Arg Lys Pro Arg
65                  70                  75                  80
Lys Ala Ala Thr Gln Glu Lys Val Lys Ser Lys Glu Thr Gly Ser Ala
                85                  90                  95
Lys Lys Lys Asn Leu Lys Glu Ser Ala Thr Lys Lys Pro Ala Asn Val
            100                 105                 110
Gly Asp Met Ser Asn Lys Ser Pro Glu Val Thr Leu Lys Ser Cys Arg
        115                 120                 125
Lys Ala Leu Asn Phe Asp Leu Glu Asn Pro Gly Asp Ala Arg Gln Gly
130                 135                 140
Asp Ser Glu Ser Glu Ile Val Gln Asn Ser Ser Gly Ala Asn Ser Phe
145                 150                 155                 160
Ser Glu Ile Arg Asp Ala Ile Gly Gly Thr Asn Gly Ser Phe Leu Asp
                165                 170                 175
Ser Val Ser Gln Ile Asp Lys Thr Asn Gly Leu Gly Ala Met Asn Gln
            180                 185                 190
Pro Leu Glu Val Ser Met Gly Asn Gln Pro Asp Lys Leu Ser Thr Gly
        195                 200                 205
Ala Lys Leu Ala Arg Asp Gln Gln Pro Asp Leu Leu Thr Arg Asn Gln
210                 215                 220
Gln Cys Gln Phe Pro Val Ala Thr Gln Asn Thr Gln Phe Pro Met Glu
225                 230                 235                 240
Asn Gln Gln Ala Trp Leu Gln Met Lys Asn Gln Leu Ile Gly Phe Pro
                245                 250                 255
Phe Gly Asn Gln Gln Pro Arg Met Thr Ile Arg Asn Gln Gln Pro Cys
            260                 265                 270
Leu Ala Met Gly Asn Gln Gln Pro Met Tyr Leu Ile Gly Thr Pro Arg
        275                 280                 285
Pro Ala Leu Val Ser Gly Asn Gln Gln Leu Gly Gly Pro Gln Gly Asn
        290                 295                 300
Lys Arg Pro Ile Phe Leu Asn His Gln Thr Cys Leu Pro Ala Gly Asn
305                 310                 315                 320
Gln Leu Tyr Gly Ser Pro Thr Asp Met His Gln Leu Val Met Ser Thr
                325                 330                 335
Gly Gly Gln Gln His Gly Leu Leu Ile Lys Asn Gln Gln Pro Gly Ser
            340                 345                 350
Leu Ile Arg Gly Gln Gln Pro Cys Val Pro Leu Ile Asp Gln Gln Pro
        355                 360                 365
Ala Thr Pro Lys Gly Phe Thr His Leu Asn Gln Met Val Ala Thr Ser
370                 375                 380
```

```
Met Ser Ser Pro Gly Leu Arg Pro His Ser Gln Ser Gln Val Pro Thr
385                 390                 395                 400

Thr Tyr Leu His Val Glu Ser Val Ser Arg Ile Leu Asn Gly Thr Thr
            405                 410                 415

Gly Thr Cys Gln Arg Ser Arg Ala Pro Ala Tyr Asp Ser Leu Gln Gln
                420                 425                 430

Asp Ile His Gln Gly Asn Lys Tyr Ile Leu Ser His Glu Ile Ser Asn
            435                 440                 445

Gly Asn Gly Cys Lys Lys Ala Leu Pro Gln Asn Ser Ser Leu Pro Thr
        450                 455                 460

Pro Ile Met Ala Lys Leu Glu Glu Ala Arg Gly Ser Lys Arg Gln Tyr
465                 470                 475                 480

His Arg Ala Met Gly Gln Thr Glu Lys His Asp Leu Asn Leu Ala Gln
                485                 490                 495

Gln Ile Ala Gln Ser Gln Asp Val Glu Arg His Asn Ser Ser Thr Cys
                500                 505                 510

Val Glu Tyr Leu Asp Ala Ala Lys Lys Thr Lys Ile Gln Lys Val Val
            515                 520                 525

Gln Glu Asn Leu His Gly Met Pro Pro Glu Val Ile Glu Ile Glu Asp
        530                 535                 540

Asp Pro Thr Asp Gly Ala Arg Lys Gly Lys Asn Thr Ala Ser Ile Ser
545                 550                 555                 560

Lys Gly Ala Ser Lys Gly Asn Ser Ser Pro Val Lys Lys Thr Ala Glu
                565                 570                 575

Lys Glu Lys Cys Ile Val Pro Lys Thr Pro Ala Lys Lys Gly Arg Ala
                580                 585                 590

Gly Arg Lys Lys Ser Val Pro Pro Ala His Ala Ser Glu Ile Gln
            595                 600                 605

Leu Trp Gln Pro Thr Pro Pro Lys Thr Pro Leu Ser Arg Ser Lys Pro
        610                 615                 620

Lys Gly Lys Gly Arg Lys Ser Ile Gln Asp Ser Gly Lys Ala Arg Gly
625                 630                 635                 640

Pro Ser Gly Glu Leu Leu Cys Gln Asp Ser Ile Ala Glu Ile Ile Tyr
                645                 650                 655

Arg Met Gln Asn Leu Tyr Leu Gly Asp Lys Glu Arg Glu Gln Glu Gln
                660                 665                 670

Asn Ala Met Val Leu Tyr Lys Gly Asp Gly Ala Leu Val Pro Tyr Glu
            675                 680                 685

Ser Lys Lys Arg Lys Pro Arg Pro Lys Val Asp Ile Asp Asp Glu Thr
        690                 695                 700

Thr Arg Ile Trp Asn Leu Leu Met Gly Lys Gly Asp Glu Lys Glu Gly
705                 710                 715                 720

Asp Glu Glu Lys Asp Lys Lys Glu Lys Trp Trp Glu Glu Arg
                725                 730                 735

Arg Val Phe Arg Gly Arg Ala Asp Ser Phe Ile Ala Arg Met His Leu
                740                 745                 750

Val Gln Gly Asp Arg Arg Phe Ser Pro Trp Lys Gly Ser Val Val Asp
            755                 760                 765

Ser Val Ile Gly Val Phe Leu Thr Gln Asn Val Ser Asp His Leu Ser
        770                 775                 780

Ser Ser Ala Phe Met Ser Leu Ala Ala Arg Phe Pro Pro Lys Leu Ser
785                 790                 795                 800

Ser Ser Arg Glu Asp Glu Arg Asn Val Arg Ser Val Val Val Glu Asp
```

-continued

```
                805                 810                 815
Pro Glu Gly Cys Ile Leu Asn Leu Asn Glu Ile Pro Ser Trp Gln Glu
                820                 825                 830
Lys Val Gln His Pro Ser Asp Met Glu Val Ser Gly Val Asp Ser Gly
            835                 840                 845
Ser Lys Glu Gln Leu Arg Asp Cys Ser Asn Ser Gly Ile Glu Arg Phe
        850                 855                 860
Asn Phe Leu Glu Lys Ser Ile Gln Asn Leu Glu Glu Val Leu Ser
865                 870                 875                 880
Ser Gln Asp Ser Phe Asp Pro Ala Ile Phe Gln Ser Cys Gly Arg Val
                885                 890                 895
Gly Ser Cys Ser Cys Ser Lys Ser Asp Ala Glu Phe Pro Thr Thr Arg
            900                 905                 910
Cys Glu Thr Lys Thr Val Ser Gly Thr Ser Gln Ser Val Gln Thr Gly
        915                 920                 925
Ser Pro Asn Leu Ser Asp Glu Ile Cys Leu Gln Gly Asn Glu Arg Pro
    930                 935                 940
His Leu Tyr Glu Gly Ser Gly Asp Val Gln Lys Gln Glu Thr Thr Asn
945                 950                 955                 960
Val Ala Gln Lys Lys Pro Asp Leu Glu Lys Thr Met Asn Trp Lys Asp
                965                 970                 975
Ser Val Cys Phe Gly Gln Pro Arg Asn Asp Thr Asn Trp Gln Thr Thr
            980                 985                 990
Pro Ser Ser Ser Tyr Glu Gln Cys Ala Thr Arg Gln Pro His Val Leu
        995                 1000                1005
Asp Ile Glu Asp Phe Gly Met Gln Gly Glu Gly Leu Gly Tyr Ser Trp
    1010                1015                1020
Met Ser Ile Ser Pro Arg Val Asp Arg Val Lys Asn Lys Asn Val Pro
1025                1030                1035                1040
Arg Arg Phe Phe Arg Gln Gly Gly Ser Val Pro Arg Glu Phe Thr Gly
                1045                1050                1055
Gln Ile Ile Pro Ser Thr Pro His Glu Leu Pro Gly Met Gly Leu Ser
            1060                1065                1070
Gly Ser Ser Ser Ala Val Gln Glu His Gln Asp Asp Thr Gln His Asn
        1075                1080                1085
Gln Gln Asp Glu Met Asn Lys Ala Ser His Leu Gln Lys Thr Phe Leu
    1090                1095                1100
Asp Leu Leu Asn Ser Ser Glu Glu Cys Leu Thr Arg Gln Ser Ser Thr
1105                1110                1115                1120
Lys Gln Asn Ile Thr Asp Gly Cys Leu Pro Arg Asp Arg Thr Ala Glu
                1125                1130                1135
Asp Val Val Asp Pro Leu Ser Asn Asn Ser Ser Leu Gln Asn Ile Leu
            1140                1145                1150
Val Glu Ser Asn Ser Ser Asn Lys Glu Gln Thr Ala Val Glu Tyr Lys
        1155                1160                1165
Glu Thr Asn Ala Thr Ile Leu Arg Glu Met Lys Gly Thr Leu Ala Asp
    1170                1175                1180
Gly Lys Lys Pro Thr Ser Gln Trp Asp Ser Leu Arg Lys Asp Val Glu
1185                1190                1195                1200
Gly Asn Glu Gly Arg Gln Glu Arg Asn Lys Asn Asn Met Asp Ser Ile
                1205                1210                1215
Asp Tyr Glu Ala Ile Arg Arg Ala Ser Ile Ser Glu Ile Ser Glu Ala
    1220                1225                1230
```

-continued

```
Ile Lys Glu Arg Gly Met Asn Asn Met Leu Ala Val Arg Ile Lys Asp
        1235                1240                1245
Phe Leu Glu Arg Ile Val Lys Asp His Gly Ile Asp Leu Glu Trp
    1250                1255                1260
Leu Arg Glu Ser Pro Pro Asp Lys Ala Lys Asp Tyr Leu Leu Ser Ile
1265            1270                1275                    1280
Arg Gly Leu Gly Leu Lys Ser Val Glu Cys Val Arg Leu Leu Thr Leu
            1285                1290                1295
His Asn Leu Ala Phe Pro Val Asp Thr Asn Val Gly Arg Ile Ala Val
        1300                1305                1310
Arg Met Gly Trp Val Pro Leu Gln Pro Leu Pro Glu Ser Leu Gln Leu
        1315                1320                1325
His Leu Leu Glu Leu Tyr Pro Val Leu Glu Ser Ile Gln Lys Phe Leu
        1330                1335                1340
Trp Pro Arg Leu Cys Lys Leu Asp Gln Arg Thr Leu Tyr Glu Leu His
1345                1350                1355                1360
Tyr Gln Leu Ile Thr Phe Gly Lys Val Phe Cys Thr Lys Ser Arg Pro
            1365                1370                1375
Asn Cys Asn Ala Cys Pro Met Arg Gly Glu Cys Arg His Phe Ala Ser
            1380                1385                1390
Ala Tyr Ala Ser Ala Arg Leu Ala Leu Pro Ala Pro Glu Glu Arg Ser
        1395                1400                1405
Leu Thr Ser Ala Thr Ile Pro Val Pro Pro Glu Ser Phe Pro Pro Val
        1410                1415                1420
Ala Ile Pro Met Ile Glu Leu Pro Leu Pro Leu Glu Lys Ser Leu Ala
1425                1430                1435                1440
Ser Gly Ala Pro Ser Asn Arg Glu Asn Cys Glu Pro Ile Ile Glu Glu
            1445                1450                1455
Pro Ala Ser Pro Gly Gln Glu Cys Thr Glu Ile Thr Glu Ser Asp Ile
            1460                1465                1470
Glu Asp Ala Tyr Tyr Asn Glu Asp Pro Asp Glu Ile Pro Thr Ile Lys
            1475                1480                1485
Leu Asn Ile Glu Gln Phe Gly Met Thr Leu Arg Glu His Met Glu Arg
    1490                1495                1500
Asn Met Glu Leu Gln Glu Gly Asp Met Ser Lys Ala Leu Val Ala Leu
1505                1510                1515                1520
His Pro Thr Thr Thr Ser Ile Pro Thr Pro Lys Leu Lys Asn Ile Ser
                1525                1530                1535
Arg Leu Arg Thr Glu His Gln Val Tyr Glu Leu Pro Asp Ser His Arg
            1540                1545                1550
Leu Leu Asp Gly Met Asp Lys Arg Glu Pro Asp Asp Pro Ser Pro Tyr
            1555                1560                1565
Leu Leu Ala Ile Trp Thr Pro Gly Glu Thr Ala Asn Ser Ala Gln Pro
    1570                1575                1580
Pro Glu Gln Lys Cys Gly Gly Lys Ala Ser Gly Lys Met Cys Phe Asp
1585                1590                1595                1600
Glu Thr Cys Ser Glu Cys Asn Ser Leu Arg Glu Ala Asn Ser Gln Thr
            1605                1610                1615
Val Arg Gly Thr Leu Leu Ile Pro Cys Arg Thr Ala Met Arg Gly Ser
            1620                1625                1630
Phe Pro Leu Asn Gly Thr Tyr Phe Gln Val Asn Glu Leu Phe Ala Asp
            1635                1640                1645
```

```
His Glu Ser Ser Leu Lys Pro Ile Asp Val Pro Arg Asp Trp Ile Trp
    1650                1655                1660
Asp Leu Pro Arg Arg Thr Val Tyr Phe Gly Thr Ser Val Thr Ser Ile
1665                1670                1675                1680
Phe Arg Gly Leu Ser Thr Glu Gln Ile Gln Phe Cys Phe Trp Lys Gly
                1685                1690                1695
Phe Val Cys Val Arg Gly Phe Glu Gln Lys Thr Arg Ala Pro Arg Pro
            1700                1705                1710
Leu Met Ala Arg Leu His Phe Pro Ala Ser Lys Leu Lys Asn Asn Lys
        1715                1720                1725
Thr

<210> SEQ ID NO 3
<211> LENGTH: 3424
<212> TYPE: DNA
<213> ORGANISM: Arabidopsis sp.
<220> FEATURE:
<223> OTHER INFORMATION: ATROPOS (ATR) 5' flanking sequence

<400> SEQUENCE: 3
```

| | | | | | |
|---|---|---|---|---|---|
| aagcttaaag | ctaccaacat | cgaatttagt | aaaagaccca | tgatttgaaa | ttggaattgt | 60 |
| cggcaaaatc | gagaagatat | agagccgaca | cgggaacagt | gaaaaccaca | aagcgcgtaa | 120 |
| gaatgaaaca | gtgggagaag | gaagagagaa | tcttaccgat | cattcgaggg | aaaagatggg | 180 |
| aatcagagaa | aaatctggaa | aaaagaaat | taagagaaag | agagaagaa | aagtgaggag | 240 |
| gaagatgcag | tgaagactgc | tatagccaca | tcccacatgg | tgtgatgaga | gagagagaga | 300 |
| gagaggttaa | agcagcaaat | tgtggagaga | taaagagaga | gagagactga | gcgagtcaag | 360 |
| ttcgtcgtcg | tgtttaaaag | aaagaatcct | atatttgcct | ttttctttac | tactttattt | 420 |
| tcagactatt | tgcttatttt | gcctcaaact | ttttgattg | tcacttttcg | atcctaaagt | 480 |
| gtttgacaat | ttacctgcct | ttttctccaa | gaaaaatcag | aacagaccac | agcaaattta | 540 |
| tgtattttct | attaaaaaag | aaagaaagaa | ttcatattac | ttatagaatt | aaaagctaag | 600 |
| cagttgaaaa | cgtgaaagca | gaatttctaa | aaaaaatagt | aaactgctac | aaacttattt | 660 |
| atgtgtatat | aacatatcta | taaagaaact | caaatatatg | ataaatcatt | ttaacaaaat | 720 |
| ttctatgaaa | ttataataaa | aaagtcact | tttgacactt | aaaaggttga | caataaccgt | 780 |
| ctctccaaaa | aaaatcaaa | acatttataa | tttctaaaac | tatggtgtaa | ttttgctgaa | 840 |
| atcaaaaaga | aagaaggat | ttctatatca | taagtttcat | tattgtatca | aactttcaaa | 900 |
| tttcatgtaa | tttgaaagga | aaaaattaa | gatataatgt | tgtttttgtt | tcttatgtta | 960 |
| cattttcatg | gaatatatat | tcataacaaa | aaatgtattt | taatatgatg | agagattacc | 1020 |
| atccaaaagg | tcgaacttat | ataaaacaag | ttaataacta | aacaatacat | gtgatcacaa | 1080 |
| tcaatgacag | ttttgatctt | aaaatagaaa | tgattgagca | aacctcaaaa | atgtcttctt | 1140 |
| aggatcacaa | aatctttcct | ttagcttatt | aaagccggga | gttcaactct | ctctcccttg | 1200 |
| tagacttttt | gttttcaaat | cttttctctt | caaaaaatca | ataattagtt | aatgggcata | 1260 |
| atatttggtt | ttaattaagt | ccatagattt | tttaggacca | tctctaatca | cgacaaatat | 1320 |
| cctaaattgt | aacacattta | aaacttaaaa | gtattgcatt | cacaatcctt | aaaatatata | 1380 |
| tatatatata | tatatatata | tatatatata | tatatgaaag | ttatatagaa | acgataactc | 1440 |
| cttactcaac | aattagccca | aaaaacatc | cataatgcat | ttaaactagg | aattttaaca | 1500 |
| aactcaaata | ggttggtagt | taaaaaaaaa | caaatagtag | atgtacatac | gtacctttaa | 1560 |

-continued

```
aaatatatac tcatatcgaa agttttaaat tttgcgaaat taaatacatt tatctatcaa    1620
ttaaaataca tttaataatg cataattctg taatatctat ctttaatttc catatagaac    1680
caaaacaaaa taaacatatc aaatagtttt aacttaacaa aaacgttagg gaaaagttga    1740
cctaactagc ttgattgacg ttgaacttgt caatgcgaaa gcgatatttc caatatatac    1800
tacatgtagt attatttata tggaagtttc taaaaaggtg ttgagtggat tgttacttgt    1860
tggaggatgc tatttttttcc ttcttgccat aatatttac gagtatggga taactacata    1920
ctcatgatta tgaaacgctc actttatttg aaaaacctcc taatacacca aatatgtcac    1980
tagattccaa aacgtagacc aattgtatct aatctcaaat tctcaatcaa agtattaatt    2040
taccgatggt aagaaaagtt aaccgatata attatcaaaa gaaagaataa gtcaacagat    2100
tcttaatctc tttattttgg tatatgaaca tttgtacaaa aatctcaaaa gatatgtaac    2160
tgtttaaaat ataaattcac tgagattaat tcttcagact cgtgttagct ataataatgt    2220
caagagttct tcttgtttca aggaaaaacc ttaaagatat gtatattttc tgtaattatg    2280
atgatataat ttgctattca ttgtcacaaa cattacttta aaaaatcgta ttttcattac    2340
tacaatgttg actaagaaca aaaatacatt gattattgat atatcgtcaa ctgaattttc    2400
ttccgaggga tataattctc aaacatagca agaatctcat aataatgttt cgtgactacc    2460
tttagacgaa attttttttaa gattcgtaac gtgacttatg gtctcttgct gtggggtca    2520 atgcgaataa atctaaatgt atgggagtca aataaaatac caagaaaaat aaaggagcag    2580
cacccaataa actatatggg accagaaatc ctttcattgg tttaaaatag gattatcccg    2640
aaagatgaag gactaaattg aaactgattg ggggtaggaa gagatccgtc acaatcatta    2700
atggcttcca cgcggaaact tgtcgtttat acaatttcat taactttcgg gtcgggttta    2760
tattccaaat gggtcaaata atattagttt aatacactaa cggagtaatt aattggtgac    2820
tacaatttta tcagtttggt gcaattagaa acgaacatag tcgtaaaata cgagttcggt    2880 gttataccttt tatttacgtt aaaaaaatac gagaattttg tgtcaaattt caaattaatt    2940
tcatgaatat atggaaatta ttagatactc tagcgaaaat agtgattatg agcgttttac    3000
aaaaatacga ttttagcatt gaacttcctt tatgtaattc ggtcaaatgt tggcatgaag    3060
aagcaagttt gcaacattaa atttcattta aaaatcgtgt tgacatactt taaaatctaa    3120
atataggaag aagaccaaaa cattaaattt agtaagattc taatgaacat ttataagtta    3180
taacttataa ccaacaaaag ttgggtttag cgttgttgct ttatctgaaa acttgcaaac    3240
taaaccattt taataggact aatgacaatt aacaacaaaa tacacttaag caacaacgtc    3300
ctcgtgaata taatttgggc ctcaggccca tattgctaac gccaactgat atttcacttt    3360
attccttctt catctcacca cactctctct ctatctctat ctctaacggc atagctgact    3420
cagt                                                                3424
```

<210> SEQ ID NO 4
<211> LENGTH: 205
<212> TYPE: DNA
<213> ORGANISM: Arabidopsis sp.
<220> FEATURE:
<223> OTHER INFORMATION: ATROPOS (ATR) 3' flanking sequence

<400> SEQUENCE: 4

```
agatgactgg aagaaagcaa acgcattgct tctctgctct cctctatttta aagccaggaa      60 aagtcccatt tagacataat aacaggaatc caaataggct attttctctt tctttcttat     120
ttcattcata gagcagaagc gacacaaaaa agttttttgg gttatttatt ttctctctaa     180
```

```
caaaaaaaaa aaaaaaaaac tcgag                                              205

<210> SEQ ID NO 5
<211> LENGTH: 6873
<212> TYPE: DNA
<213> ORGANISM: Arabidopsis sp.
<220> FEATURE:
<223> OTHER INFORMATION: ATROPOS (ATR) cDNA sequence
<221> NAME/KEY: CDS
<222> LOCATION: (1479)...(6668)
<223> OTHER INFORMATION: ATROPOS (ATR) polypeptide

<400> SEQUENCE: 5
gttctccggc attgactcgc ctgagaatca gaaagcttag atcggtgagc ttttagctcc         60
attttctgtt tatttacata ttatttcctt tttttctctc tccctttttt atctggaatt        120
tgttctgcta aattttccag ctgttacatt ttccgatcac gagaagaatc actgggtttt        180
tatgttaatc aatacatgtt cctgttttct gatcataaat ctcagctatt aacacctgat        240
tttgattctg cgtaataaaa acctctgatt gcttttatc ttcactttcc ccataaacat         300
tgcttacttt attcgctctt cttttaccgt ttccagctaa aaaattcttc gctattcaat        360
gtgtttctcg ttttgttgat gagaaaaata tctgacaaaa aatcatttat tgcattttat        420
ggtgcagatt cttagttaat gtcgccttct ctaaccaagt cagattaaaa aggagtgttc        480
gtccatgttg ctttgttttg gtgtttggag agagttttcg gagagttagg tgagtgttat        540
ttggggtgag gtagtgataa ggtttgaagg gggagtgatt catcaagtgt gttatgaatt        600
cgagggctga tccggggat agatattttc gagttccttt ggagaatcaa actcaacaag         660
agttcatggg ttcttggatt ccatttacac ccaaaaaacc tagatcaagt ctgatggtag        720
atgagagagt gataaaccag gatctaaatg ggtttccagg tggtgaattt gtagacaggg        780
gattctgcaa cactggtgtg gatcataatg gggttttga tcatggtgct catcagggcg         840
ttaccaactt aagtatgatg atcaatagct tagcgggatc acatgcacaa gcttggagta        900
atagtgagag agatcttttg ggcaggagtg aggtgacttc tcctttagca ccagttatca        960
gaaacaccac cggtaatgta gagccggtca atggaaattt tacttcagat gtgggtatgg       1020
taaatggtcc tttcacccag agtggcactt ctcaagctgg ctataatgag tttgaattgg       1080
atgacttgtt gaatcctgat cagatgccct ctccttcac aagcttgctg agtggtgggg        1140
atagcttatt caaggttcgt caatgtgagt gatcaaatct attttcagtt tttttttttc       1200
cctttcttcc gttcttgcag tacttagagt agaacatgaa ttagaatatc ttaagaaagt       1260
catggttttg aacagatgga cctccagcgt gtaacaagcc tctttacaat ttgaattcac       1320
caattagaag agaagcagtt gggtcagtct gtgaaagttc gtttcaatat gtaccgtcaa       1380
cgcccagtct gttcagaaca ggtgaaaaga ctggattcct tgaacagata gttacaacta       1440
ctggacatga atcccagag ccgaaatctg acaaaagt atg cag agc att atg gac       1496
                                             Met Gln Ser Ile Met Asp
                                              1               5 tcg tct gct gtt aat gcg acg gaa gct act gaa caa aat gat ggc agc       1544
Ser Ser Ala Val Asn Ala Thr Glu Ala Thr Glu Gln Asn Asp Gly Ser
           10                  15                  20 aga caa gat gtt ctg gag ttc gac ctt aac aaa act cct cag cag aaa       1592
Arg Gln Asp Val Leu Glu Phe Asp Leu Asn Lys Thr Pro Gln Gln Lys
        25                  30                  35 ccc tcc aaa agg aaa agg aag ttc atg ccc aag gtg gtc gtg gaa ggc       1640
Pro Ser Lys Arg Lys Arg Lys Phe Met Pro Lys Val Val Val Glu Gly
    40                  45                  50
```

```
                                                                -continued aaa cct aaa aga aag cca cgc aaa cct gca gaa ctt ccc aaa gtg gtc      1688
Lys Pro Lys Arg Lys Pro Arg Lys Pro Ala Glu Leu Pro Lys Val Val
 55              60                  65                  70 gtg gaa ggc aaa cct aaa agg aag cca cgc aaa gct gca act cag gaa      1736
Val Glu Gly Lys Pro Lys Arg Lys Pro Arg Lys Ala Ala Thr Gln Glu
                 75                  80                  85 aaa gtg aaa tct aaa gaa acc ggg agt gcc aaa aag aaa aat ttg aaa      1784
Lys Val Lys Ser Lys Glu Thr Gly Ser Ala Lys Lys Lys Asn Leu Lys
             90                  95                 100 gaa tca gca act aaa aag cca gcc aat gtt gga gat atg agc aac aaa      1832
Glu Ser Ala Thr Lys Lys Pro Ala Asn Val Gly Asp Met Ser Asn Lys
        105                 110                 115 agc cct gaa gtc aca ctc aaa agt tgc aga aaa gct ttg aat ttt gac      1880
Ser Pro Glu Val Thr Leu Lys Ser Cys Arg Lys Ala Leu Asn Phe Asp
    120                 125                 130 ttg gag aat cct gga gat gcg agg caa ggt gac tct gag tct gaa att      1928
Leu Glu Asn Pro Gly Asp Ala Arg Gln Gly Asp Ser Glu Ser Glu Ile
135                 140                 145                 150 gtc cag aac agt agt ggc gca aac tcg ttt tct gag atc aga gat gcc      1976
Val Gln Asn Ser Ser Gly Ala Asn Ser Phe Ser Glu Ile Arg Asp Ala
                155                 160                 165 att ggt gga act aat ggt agt ttc ctg gat tca gtg tca caa ata gac      2024
Ile Gly Gly Thr Asn Gly Ser Phe Leu Asp Ser Val Ser Gln Ile Asp
            170                 175                 180 aag acc aat gga ttg ggg gct atg aac cag cca ctt gaa gtg tca atg      2072
Lys Thr Asn Gly Leu Gly Ala Met Asn Gln Pro Leu Glu Val Ser Met
        185                 190                 195 gga aac cag cca gat aaa cta tct aca gga gcg aaa ctg gcc aga gac      2120
Gly Asn Gln Pro Asp Lys Leu Ser Thr Gly Ala Lys Leu Ala Arg Asp
    200                 205                 210 caa caa cct gat tta ttg act aga aac cag caa tgc cag ttc cca gtg      2168
Gln Gln Pro Asp Leu Leu Thr Arg Asn Gln Gln Cys Gln Phe Pro Val
215                 220                 225                 230 gca acc cag aac acc cag ttc cca atg gaa aac caa caa gct tgg ctt      2216
Ala Thr Gln Asn Thr Gln Phe Pro Met Glu Asn Gln Gln Ala Trp Leu
                235                 240                 245 cag atg aaa aac caa ctt att ggc ttt cca ttt ggt aac cag caa cct      2264
Gln Met Lys Asn Gln Leu Ile Gly Phe Pro Phe Gly Asn Gln Gln Pro
            250                 255                 260 cgc atg acc ata aga aac cag cag cct tgc ttg gcc atg ggt aat caa      2312
Arg Met Thr Ile Arg Asn Gln Gln Pro Cys Leu Ala Met Gly Asn Gln
        265                 270                 275 caa cct atg tat ctg ata gga act cca cgg cct gca tta gta agt gga      2360
Gln Pro Met Tyr Leu Ile Gly Thr Pro Arg Pro Ala Leu Val Ser Gly
    280                 285                 290 aac cag caa cta gga ggt ccc caa gga aac aag cgg cct ata ttt ttg      2408
Asn Gln Gln Leu Gly Gly Pro Gln Gly Asn Lys Arg Pro Ile Phe Leu
295                 300                 305                 310 aat cac cag act tgt tta cct gct gga aat cag cta tat gga tca cct      2456
Asn His Gln Thr Cys Leu Pro Ala Gly Asn Gln Leu Tyr Gly Ser Pro
                315                 320                 325 aca gac atg cat caa ctt gtt atg tca acc gga ggg caa caa cat gga      2504
Thr Asp Met His Gln Leu Val Met Ser Thr Gly Gly Gln Gln His Gly
            330                 335                 340 cta ctg ata aaa aac cag caa cct gga tca tta ata aga ggc cag cag      2552
Leu Leu Ile Lys Asn Gln Gln Pro Gly Ser Leu Ile Arg Gly Gln Gln
        345                 350                 355 cct tgc gta cct ttg att gac cag caa cct gca act cca aaa ggt ttt      2600
Pro Cys Val Pro Leu Ile Asp Gln Gln Pro Ala Thr Pro Lys Gly Phe
```

```
        360                 365                 370
act cac ttg aat cag atg gta gct acc agc atg tca tcg cct ggg ctt    2648
Thr His Leu Asn Gln Met Val Ala Thr Ser Met Ser Ser Pro Gly Leu
375                 380                 385                 390 cga cct cat tct cag tca caa gtt cct aca aca tat cta cat gtg gaa    2696
Arg Pro His Ser Gln Ser Gln Val Pro Thr Thr Tyr Leu His Val Glu
                395                 400                 405 tct gtt tcc agg att ttg aat ggg act aca ggt aca tgc cag aga agc    2744
Ser Val Ser Arg Ile Leu Asn Gly Thr Thr Gly Thr Cys Gln Arg Ser
            410                 415                 420 agg gct cct gca tac gat tct tta cag caa gat atc cat caa gga aat    2792
Arg Ala Pro Ala Tyr Asp Ser Leu Gln Gln Asp Ile His Gln Gly Asn
        425                 430                 435 aag tac ata ctt tct cat gag ata tcc aat ggt aat ggg tgc aag aaa    2840
Lys Tyr Ile Leu Ser His Glu Ile Ser Asn Gly Asn Gly Cys Lys Lys
    440                 445                 450 gcg tta cct caa aac tct tct ctg cca act cca att atg gct aaa ctt    2888
Ala Leu Pro Gln Asn Ser Ser Leu Pro Thr Pro Ile Met Ala Lys Leu
455                 460                 465                 470 gag gaa gcc agg ggc tcg aag aga cag tat cat cgt gca atg gga cag    2936
Glu Glu Ala Arg Gly Ser Lys Arg Gln Tyr His Arg Ala Met Gly Gln
                475                 480                 485 acg gaa aag cat gat cta aac tta gct caa cag att gct caa tca caa    2984
Thr Glu Lys His Asp Leu Asn Leu Ala Gln Gln Ile Ala Gln Ser Gln
            490                 495                 500 gat gtg gag aga cat aac agc agc acg tgt gtg gaa tat tta gat gct    3032
Asp Val Glu Arg His Asn Ser Ser Thr Cys Val Glu Tyr Leu Asp Ala
        505                 510                 515 gca aag aaa acg aaa atc cag aaa gta gtc caa gaa aat ttg cat ggc    3080
Ala Lys Lys Thr Lys Ile Gln Lys Val Val Gln Glu Asn Leu His Gly
    520                 525                 530 atg cca cct gag gtt ata gaa atc gag gat gat cca act gat ggg gca    3128
Met Pro Pro Glu Val Ile Glu Ile Glu Asp Asp Pro Thr Asp Gly Ala
535                 540                 545                 550 aga aaa ggt aaa aat act gcc agc atc agt aaa ggt gca tct aaa gga    3176
Arg Lys Gly Lys Asn Thr Ala Ser Ile Ser Lys Gly Ala Ser Lys Gly
                555                 560                 565 aac tcg tct cca gtt aaa aag aca gca gaa aag gag aaa tgt att gtc    3224
Asn Ser Ser Pro Val Lys Lys Thr Ala Glu Lys Glu Lys Cys Ile Val
            570                 575                 580 cca aaa acg cct gca aaa aag ggt cga gca ggt aga aaa aaa tca gta    3272
Pro Lys Thr Pro Ala Lys Lys Gly Arg Ala Gly Arg Lys Lys Ser Val
        585                 590                 595 cct ccg cct gct cat gcc tca gag atc cag ctt tgg caa cct act cct    3320
Pro Pro Pro Ala His Ala Ser Glu Ile Gln Leu Trp Gln Pro Thr Pro
    600                 605                 610 cca aag aca cct tta tca aga agc aag cct aaa gga aaa ggg aga aag    3368
Pro Lys Thr Pro Leu Ser Arg Ser Lys Pro Lys Gly Lys Gly Arg Lys
615                 620                 625                 630 tcc ata caa gat tca gga aaa gca aga ggt cca tca gga gaa ctt ctg    3416
Ser Ile Gln Asp Ser Gly Lys Ala Arg Gly Pro Ser Gly Glu Leu Leu
                635                 640                 645 tgt cag gat tct att gcg gaa ata att tac agg atg caa aat ctg tat    3464
Cys Gln Asp Ser Ile Ala Glu Ile Ile Tyr Arg Met Gln Asn Leu Tyr
            650                 655                 660 cta gga gac aaa gaa aga gaa caa gag caa aat gca atg gtc ttg tac    3512
Leu Gly Asp Lys Glu Arg Glu Gln Glu Gln Asn Ala Met Val Leu Tyr
        665                 670                 675 aaa gga gat ggt gca ctt gtt ccc tat gag agc aag aag cga aaa cca    3560
```

-continued

| | | |
|---|---|---|
| Lys Gly Asp Gly Ala Leu Val Pro Tyr Glu Ser Lys Lys Arg Lys Pro<br>680                         685                      690 | | |
| aga ccc aaa gtt gac att gac gat gaa aca act cgc ata tgg aac tta<br>Arg Pro Lys Val Asp Ile Asp Asp Glu Thr Thr Arg Ile Trp Asn Leu<br>695                     700                   705                   710 | | 3608 |
| ctg atg ggg aaa gga gat gaa aaa gaa ggg gat gaa gag aag gat aaa<br>Leu Met Gly Lys Gly Asp Glu Lys Glu Gly Asp Glu Glu Lys Asp Lys<br>               715                   720                   725 | | 3656 |
| aag aaa gag aag tgg tgg gaa gaa gaa aga aga gtc ttc cga gga agg<br>Lys Lys Glu Lys Trp Trp Glu Glu Glu Arg Arg Val Phe Arg Gly Arg<br>               730                   735                   740 | | 3704 |
| gct gat tcc ttc atc gct cgc atg cac ctg gta caa gga gat aga cgt<br>Ala Asp Ser Phe Ile Ala Arg Met His Leu Val Gln Gly Asp Arg Arg<br>               745                   750                   755 | | 3752 |
| ttt tcg cca tgg aag gga tcg gtg gtt gat tcg gtc att gga gtt ttc<br>Phe Ser Pro Trp Lys Gly Ser Val Val Asp Ser Val Ile Gly Val Phe<br>760                         765                   770 | | 3800 |
| ctt aca cag aat gtc tcg gat cac ctt tca agc tct gcg ttc atg tct<br>Leu Thr Gln Asn Val Ser Asp His Leu Ser Ser Ser Ala Phe Met Ser<br>775                     780                   785                   790 | | 3848 |
| cta gct gct cga ttc cct cca aaa tta agc agc agc cga gaa gat gaa<br>Leu Ala Ala Arg Phe Pro Pro Lys Leu Ser Ser Ser Arg Glu Asp Glu<br>               795                   800                   805 | | 3896 |
| agg aat gtt aga agc gta gtt gtt gaa gat cca gaa gga tgc att ctg<br>Arg Asn Val Arg Ser Val Val Val Glu Asp Pro Glu Gly Cys Ile Leu<br>               810                   815                   820 | | 3944 |
| aac tta aat gaa att cct tcg tgg cag gaa aag gtt caa cat cca tct<br>Asn Leu Asn Glu Ile Pro Ser Trp Gln Glu Lys Val Gln His Pro Ser<br>               825                   830                   835 | | 3992 |
| gac atg gaa gtt tct ggg gtt gat agt gga tca aaa gag cag cta agg<br>Asp Met Glu Val Ser Gly Val Asp Ser Gly Ser Lys Glu Gln Leu Arg<br>840                         845                   850 | | 4040 |
| gac tgt tca aac tct gga att gaa aga ttt aat ttc tta gag aag agt<br>Asp Cys Ser Asn Ser Gly Ile Glu Arg Phe Asn Phe Leu Glu Lys Ser<br>855                     860                   865                   870 | | 4088 |
| att caa aat tta gaa gag gaa gta tta tca tca caa gat tct ttt gat<br>Ile Gln Asn Leu Glu Glu Glu Val Leu Ser Ser Gln Asp Ser Phe Asp<br>               875                   880                   885 | | 4136 |
| ccg gcg ata ttt cag tcg tgt ggg aga gtt gga tcc tgt tca tgt tcc<br>Pro Ala Ile Phe Gln Ser Cys Gly Arg Val Gly Ser Cys Ser Cys Ser<br>               890                   895                   900 | | 4184 |
| aaa tca gac gca gag ttt cct aca acc agg tgt gaa aca aaa act gtc<br>Lys Ser Asp Ala Glu Phe Pro Thr Thr Arg Cys Glu Thr Lys Thr Val<br>               905                   910                   915 | | 4232 |
| agt gga aca tca caa tca gtg caa act ggg agc cca aac ttg tct gat<br>Ser Gly Thr Ser Gln Ser Val Gln Thr Gly Ser Pro Asn Leu Ser Asp<br>920                         925                   930 | | 4280 |
| gaa att tgt ctt caa ggg aat gag aga ccg cat cta tat gaa gga tct<br>Glu Ile Cys Leu Gln Gly Asn Glu Arg Pro His Leu Tyr Glu Gly Ser<br>935                     940                   945                   950 | | 4328 |
| ggt gat gtt cag aaa caa gaa act aca aat gtc gct cag aag aaa cct<br>Gly Asp Val Gln Lys Gln Glu Thr Thr Asn Val Ala Gln Lys Lys Pro<br>               955                   960                   965 | | 4376 |
| gat ctt gaa aaa aca atg aat tgg aaa gac tct gtc tgt ttt ggt cag<br>Asp Leu Glu Lys Thr Met Asn Trp Lys Asp Ser Val Cys Phe Gly Gln<br>               970                   975                   980 | | 4424 |
| cca aga aat gat act aat tgg caa aca act cct tcc agc agc tat gag<br>Pro Arg Asn Asp Thr Asn Trp Gln Thr Thr Pro Ser Ser Ser Tyr Glu<br>985                         990                   995 | | 4472 |

```
cag tgt gcg act cga cag cca cat gta cta gac ata gag gat ttt gga      4520
Gln Cys Ala Thr Arg Gln Pro His Val Leu Asp Ile Glu Asp Phe Gly
    1000                1005                1010 atg caa ggt gaa ggc ctt ggt tat tct tgg atg tcc atc tca cca aga      4568
Met Gln Gly Glu Gly Leu Gly Tyr Ser Trp Met Ser Ile Ser Pro Arg
1015                1020                1025                1030 gtt gac aga gta aag aac aaa aat gta cca cgc agg ttt ttc aga caa      4616
Val Asp Arg Val Lys Asn Lys Asn Val Pro Arg Arg Phe Phe Arg Gln
                1035                1040                1045 ggt gga agt gtt cca aga gaa ttc aca ggt cag atc ata cca tca acg      4664
Gly Gly Ser Val Pro Arg Glu Phe Thr Gly Gln Ile Ile Pro Ser Thr
            1050                1055                1060 cct cat gaa tta cca gga atg gga ttg tcc ggt tcc tca agc gcc gtc      4712
Pro His Glu Leu Pro Gly Met Gly Leu Ser Gly Ser Ser Ser Ala Val
        1065                1070                1075 caa gaa cac cag gac gat acc caa cat aat caa caa gat gag atg aat      4760
Gln Glu His Gln Asp Asp Thr Gln His Asn Gln Gln Asp Glu Met Asn
    1080                1085                1090 aaa gca tcc cat tta caa aaa aca ttt ttg gat ctg ctc aac tcc tct      4808
Lys Ala Ser His Leu Gln Lys Thr Phe Leu Asp Leu Leu Asn Ser Ser
1095                1100                1105                1110 gaa gaa tgc ctt aca aga cag tcc agt acc aaa cag aac atc acg gat      4856
Glu Glu Cys Leu Thr Arg Gln Ser Ser Thr Lys Gln Asn Ile Thr Asp
                1115                1120                1125 ggc tgt cta ccg aga gat aga act gct gaa gac gtg gtt gat ccg ctc      4904
Gly Cys Leu Pro Arg Asp Arg Thr Ala Glu Asp Val Val Asp Pro Leu
            1130                1135                1140 agt aac aat tca agc tta cag aac ata ttg gtc gaa tca aat tcc agc      4952
Ser Asn Asn Ser Ser Leu Gln Asn Ile Leu Val Glu Ser Asn Ser Ser
        1145                1150                1155 aat aaa gag cag acg gca gtt gaa tac aag gag aca aat gcc act att      5000
Asn Lys Glu Gln Thr Ala Val Glu Tyr Lys Glu Thr Asn Ala Thr Ile
    1160                1165                1170 tta cga gag atg aaa ggg acg ctt gct gat ggg aaa aag cct aca agc      5048
Leu Arg Glu Met Lys Gly Thr Leu Ala Asp Gly Lys Lys Pro Thr Ser
1175                1180                1185                1190 cag tgg gat agt ctc aga aaa gat gtg gag ggg aat gaa ggg aga cag      5096
Gln Trp Asp Ser Leu Arg Lys Asp Val Glu Gly Asn Glu Gly Arg Gln
                1195                1200                1205 gaa cga aac aaa aac aat atg gat tcc ata gac tat gaa gca ata aga      5144
Glu Arg Asn Lys Asn Asn Met Asp Ser Ile Asp Tyr Glu Ala Ile Arg
            1210                1215                1220 cgt gct agt atc agc gag att tct gag gct atc aag gaa aga ggg atg      5192
Arg Ala Ser Ile Ser Glu Ile Ser Glu Ala Ile Lys Glu Arg Gly Met
        1225                1230                1235 aat aac atg ttg gcc gta cga att aag gat ttc cta gaa cgg ata gtt      5240
Asn Asn Met Leu Ala Val Arg Ile Lys Asp Phe Leu Glu Arg Ile Val
    1240                1245                1250 aaa gat cat ggt ggt atc gac ctt gaa tgg ttg aga gaa tct cct cct      5288
Lys Asp His Gly Gly Ile Asp Leu Glu Trp Leu Arg Glu Ser Pro Pro
1255                1260                1265                1270 gat aaa gcc aag gac tat ctc ttg agc ata aga ggt ctg ggt ttg aaa      5336
Asp Lys Ala Lys Asp Tyr Leu Leu Ser Ile Arg Gly Leu Gly Leu Lys
                1275                1280                1285 agt gtt gaa tgc gtg cga ctc tta aca ctc cac aat ctt gct ttc cct      5384
Ser Val Glu Cys Val Arg Leu Leu Thr Leu His Asn Leu Ala Phe Pro
            1290                1295                1300 gtt gac acg aat gtt gga agg ata gca gtt agg atg gga tgg gtg cct      5432
Val Asp Thr Asn Val Gly Arg Ile Ala Val Arg Met Gly Trp Val Pro
        1305                1310                1315
```

```
cta caa ccc cta cct gaa tca ctt cag tta cac ctc ctg gag cta tac         5480
Leu Gln Pro Leu Pro Glu Ser Leu Gln Leu His Leu Leu Glu Leu Tyr
        1320                1325                1330 cca gtg ctc gag tcc atc caa aaa ttt ctt tgg cca aga ctt tgc aaa         5528
Pro Val Leu Glu Ser Ile Gln Lys Phe Leu Trp Pro Arg Leu Cys Lys
1335                1340                1345                1350 ctc gat caa cga aca ctg tat gaa tta cac tac caa ctg att acg ttt         5576
Leu Asp Gln Arg Thr Leu Tyr Glu Leu His Tyr Gln Leu Ile Thr Phe
                1355                1360                1365 gga aag gta ttt tgc aca aag agt aga cca aat tgt aat gca tgt cca         5624
Gly Lys Val Phe Cys Thr Lys Ser Arg Pro Asn Cys Asn Ala Cys Pro
            1370                1375                1380 atg aga gga gag tgc aga cac ttt gcc agt gct tat gct agt gca aga         5672
Met Arg Gly Glu Cys Arg His Phe Ala Ser Ala Tyr Ala Ser Ala Arg
        1385                1390                1395 ctt gct tta ccg gca cca gag gag agg agc tta aca agt gca act att         5720
Leu Ala Leu Pro Ala Pro Glu Glu Arg Ser Leu Thr Ser Ala Thr Ile
    1400                1405                1410 ccg gtc cct ccc gag tcc ttt cct cct gta gcc atc ccg atg ata gaa         5768
Pro Val Pro Pro Glu Ser Phe Pro Pro Val Ala Ile Pro Met Ile Glu
1415                1420                1425                1430 cta cct ctt ccg ttg gag aaa tcc cta gca agt gga gca cca tcg aat         5816
Leu Pro Leu Pro Leu Glu Lys Ser Leu Ala Ser Gly Ala Pro Ser Asn
                1435                1440                1445 aga gaa aac tgt gaa cca ata att gaa gag ccg gcc tcg ccc ggg caa         5864
Arg Glu Asn Cys Glu Pro Ile Ile Glu Glu Pro Ala Ser Pro Gly Gln
            1450                1455                1460 gag tgc act gaa ata acc gag agt gat att gaa gat gct tac tac aat         5912
Glu Cys Thr Glu Ile Thr Glu Ser Asp Ile Glu Asp Ala Tyr Tyr Asn
        1465                1470                1475 gag gac cct gac gag atc cca aca ata aaa ctc aac att gaa cag ttt         5960
Glu Asp Pro Asp Glu Ile Pro Thr Ile Lys Leu Asn Ile Glu Gln Phe
    1480                1485                1490 gga atg act cta cgg gaa cac atg gaa aga aac atg gag ctc caa gaa         6008
Gly Met Thr Leu Arg Glu His Met Glu Arg Asn Met Glu Leu Gln Glu
1495                1500                1505                1510 ggt gac atg tcc aag gct ttg gtt gct ttg cat cca aca act act tct         6056
Gly Asp Met Ser Lys Ala Leu Val Ala Leu His Pro Thr Thr Thr Ser
                1515                1520                1525 att cca act ccc aaa cta aag aac att agc cgt ctc agg aca gag cac         6104
Ile Pro Thr Pro Lys Leu Lys Asn Ile Ser Arg Leu Arg Thr Glu His
            1530                1535                1540 caa gtg tac gag ctc cca gat tca cat cgt ctc ctt gat ggt atg gat         6152
Gln Val Tyr Glu Leu Pro Asp Ser His Arg Leu Leu Asp Gly Met Asp
        1545                1550                1555 aaa aga gaa cca gat gat cca agt cct tat ctc tta gct ata tgg aca         6200
Lys Arg Glu Pro Asp Asp Pro Ser Pro Tyr Leu Leu Ala Ile Trp Thr
    1560                1565                1570 cca ggt gaa aca gcg aat tcg gca caa ccg cct gaa cag aag tgt gga         6248
Pro Gly Glu Thr Ala Asn Ser Ala Gln Pro Pro Glu Gln Lys Cys Gly
1575                1580                1585                1590 ggg aaa gcg tct ggc aaa atg tgc ttt gac gag act tgt tct gag tgt         6296
Gly Lys Ala Ser Gly Lys Met Cys Phe Asp Glu Thr Cys Ser Glu Cys
                1595                1600                1605 aac agt ctg agg gaa gca aac tca cag aca gtt cga gga act ctt ctg         6344
Asn Ser Leu Arg Glu Ala Asn Ser Gln Thr Val Arg Gly Thr Leu Leu
            1610                1615                1620 ata cct tgt cgg act gcc atg aga gga agt ttt ccg ctc aac ggg aca         6392
Ile Pro Cys Arg Thr Ala Met Arg Gly Ser Phe Pro Leu Asn Gly Thr
```

```
                1625                1630                1635
tat ttc caa gtc aac gag tta ttt gca gac cac gag tcc agt ctc aaa        6440
Tyr Phe Gln Val Asn Glu Leu Phe Ala Asp His Glu Ser Ser Leu Lys
        1640                1645                1650 ccc atc gat gtt cct aga gat tgg ata tgg gat ctc cca aga agg act        6488
Pro Ile Asp Val Pro Arg Asp Trp Ile Trp Asp Leu Pro Arg Arg Thr
1655                1660                1665                1670 gtt tac ttc gga aca tca gta aca tca ata ttc aga ggt ctt tca acg        6536
Val Tyr Phe Gly Thr Ser Val Thr Ser Ile Phe Arg Gly Leu Ser Thr
                1675                1680                1685 gag cag ata cag ttc tgc ttt tgg aaa gga ttc gta tgt gtc cgt gga        6584
Glu Gln Ile Gln Phe Cys Phe Trp Lys Gly Phe Val Cys Val Arg Gly
        1690                1695                1700 ttc gaa cag aag aca aga gca ccg cgt cca tta atg gca agg ttg cat        6632
Phe Glu Gln Lys Thr Arg Ala Pro Arg Pro Leu Met Ala Arg Leu His
1705                1710                1715 ttt cct gcg agc aaa ttg aag aac aac aaa acc taa agatgactgg             6678
Phe Pro Ala Ser Lys Leu Lys Asn Asn Lys Thr
        1720                1725 aagaaagcaa acgcattgct tctctgctct cctctattta aagccaggaa aagtcccatt      6738
tagacataat aacaggaatc caaataggct atttctctt tctttcttat ttcattcata       6798
gagcagaagc gacacaaaaa agttttttgg gttatttatt ttctctctaa caaaaaaaa       6858 aaaaaaaaac tcgag                                                       6873

<210> SEQ ID NO 6
<211> LENGTH: 1478
<212> TYPE: DNA
<213> ORGANISM: Arabidopsis sp.
<220> FEATURE:
<223> OTHER INFORMATION: ATROPOS (ATR) 5' untranslated region

<400> SEQUENCE: 6
gttctccggc attgactcgc ctgagaatca gaaagcttag atcggtgagc ttttagctcc        60
attttctgtt tatttacata ttatttcctt tttttctctc tccctttttt atctggaatt       120
tgttctgcta aattttccag ctgttacatt ttccgatcac gagaagaatc actgggtttt       180
tatgttaatc aatacatgtt cctgttttct gatcataaat ctcagctatt aacacctgat       240
tttgattctg cgtaataaaa acctctgatt tgcttttatc ttcactttcc ccataaacat       300
tgcttacttt attcgctctt cttttaccgt ttccagctaa aaaattcttc gctattcaat       360
gtgtttctcg ttttgttgat gagaaaaata tctgacaaaa aatcatttat tgcattttat       420
ggtgcagatt cttagttaat gtcgccttct ctaaccaagt cagattaaaa aggagtgttc       480
gtccatgttg ctttgttttg gtgtttggag agagttttcg gagagttagg tgagtgttat       540
ttggggtgag gtagtgataa ggtttgaagg gggagtgatt catcaagtgt gttatgaatt       600
cgagggctga tccgggggat agatattttc gagttccttt ggagaatcaa actcaacaag       660
agttcatggg ttcttggatt ccatttacac ccaaaaaacc tagatcaagt ctgatggtag       720
atgagagagt gataaaccag gatctaaatg ggtttccagg tggtgaattt gtagacaggg       780
gattctgcaa cactggtgtg gatcataatg gggttttga tcatggtgct catcagggcg        840
ttaccaactt aagtatgatg atcaatagct tagcgggatc acatgcacaa gcttggagta       900
atagtgagag agatcttttg ggcaggagtg aggtgacttc tcctttagca ccagttatca       960
gaaacaccac cggtaatgta gagccggtca atggaaattt tacttcagat gtgggtatgg      1020
taaatggtcc tttcacccag agtggcactt ctcaagctgg ctataatgag tttgaattgg      1080
```

```
atgacttgtt gaatcctgat cagatgccct tctccttcac aagcttgctg agtggtgggg    1140
atagcttatt caaggttcgt caatgtgagt gatcaaatct attttcagtt ttttttttc     1200 cctttcttcc gttcttgcag tacttagagt agaacatgaa ttagaatatc ttaagaaagt    1260
catggttttg aacagatgga cctccagcgt gtaacaagcc tctttacaat ttgaattcac    1320
caattagaag agaagcagtt gggtcagtct gtgaaagttc gtttcaatat gtaccgtcaa    1380
cgcccagtct gttcagaaca ggtgaaaaga ctggattcct tgaacagata gttacaacta    1440
ctggacatga aatcccagag ccgaaatctg acaaaagt                            1478
```

<210> SEQ ID NO 7
<211> LENGTH: 29
<212> TYPE: DNA
<213> ORGANISM: Artificial Sequence
<220> FEATURE:
<223> OTHER INFORMATION: primer Xba-SKEN-7

<400> SEQUENCE: 7

```
cctctagagg aattgtcggc aaaatcgag                                      29
```

<210> SEQ ID NO 8
<211> LENGTH: 22
<212> TYPE: DNA
<213> ORGANISM: Artificial Sequence
<220> FEATURE:
<223> OTHER INFORMATION: primer SKB-8

<400> SEQUENCE: 8

```
ggagagacgg ttattgtcaa cc                                             22
```

<210> SEQ ID NO 9
<211> LENGTH: 24
<212> TYPE: DNA
<213> ORGANISM: Artificial Sequence
<220> FEATURE:
<223> OTHER INFORMATION: primer SKB-7

<400> SEQUENCE: 9

```
aaaagtctac aagggagaga gagt                                           24
```

<210> SEQ ID NO 10
<211> LENGTH: 19
<212> TYPE: DNA
<213> ORGANISM: Artificial Sequence
<220> FEATURE:
<223> OTHER INFORMATION: primer SKB-5

<400> SEQUENCE: 10

```
gtagatgtac atacgtacc                                                 19
```

<210> SEQ ID NO 11
<211> LENGTH: 28
<212> TYPE: DNA
<213> ORGANISM: Artificial Sequence
<220> FEATURE:
<223> OTHER INFORMATION: primer SKEN-8

<400> SEQUENCE: 11

```
gcatcctcca acaagtaaca atccactc                                       28
```

<210> SEQ ID NO 12
<211> LENGTH: 25
<212> TYPE: DNA

<213> ORGANISM: Artificial Sequence
<220> FEATURE:
<223> OTHER INFORMATION: primer SKB-6

<400> SEQUENCE: 12
cactgagatt aattcttcag actcg                                   25

<210> SEQ ID NO 13
<211> LENGTH: 27
<212> TYPE: DNA
<213> ORGANISM: Artificial Sequence
<220> FEATURE:
<223> OTHER INFORMATION: primer SKEN-3.5

<400> SEQUENCE: 13
ctcaggcgag tcaatgccgg agaacac                                 27

<210> SEQ ID NO 14
<211> LENGTH: 29
<212> TYPE: DNA
<213> ORGANISM: Artificial Sequence
<220> FEATURE:
<223> OTHER INFORMATION: primer SKEN-3

<400> SEQUENCE: 14
cgagggctga tccgggggat agatatttt                               29

<210> SEQ ID NO 15
<211> LENGTH: 23
<212> TYPE: DNA
<213> ORGANISM: Artificial Sequence
<220> FEATURE:
<223> OTHER INFORMATION: primer SKEN-2

<400> SEQUENCE: 15
cccccggatc agccctcgaa ttc                                     23

<210> SEQ ID NO 16
<211> LENGTH: 26
<212> TYPE: DNA
<213> ORGANISM: Artificial Sequence
<220> FEATURE:
<223> OTHER INFORMATION: primer SKEN-1

<400> SEQUENCE: 16 ccctgtcta caaattcacc acctgg                                   26

<210> SEQ ID NO 17
<211> LENGTH: 21
<212> TYPE: DNA
<213> ORGANISM: Artificial Sequence
<220> FEATURE:
<223> OTHER INFORMATION: primer SKEL-4

<400> SEQUENCE: 17
ctgacccaac tgcttctctt c                                       21

<210> SEQ ID NO 18
<211> LENGTH: 22
<212> TYPE: DNA
<213> ORGANISM: Artificial Sequence
<220> FEATURE:
<223> OTHER INFORMATION: primer skes1.5

<400> SEQUENCE: 18
tcacctgttc tgaacagact gg                                      22

<210> SEQ ID NO 19
<211> LENGTH: 26
<212> TYPE: DNA
<213> ORGANISM: Artificial Sequence
<220> FEATURE:
<223> OTHER INFORMATION: primer SKES-1.4

<400> SEQUENCE: 19
cagcagacga gtccataatg ctctgc                                    26

<210> SEQ ID NO 20
<211> LENGTH: 21
<212> TYPE: DNA
<213> ORGANISM: Artificial Sequence
<220> FEATURE:
<223> OTHER INFORMATION: primer SKES-2.4

<400> SEQUENCE: 20
ggtttgcctt ccacgaccac c                                         21

<210> SEQ ID NO 21
<211> LENGTH: 27
<212> TYPE: DNA
<213> ORGANISM: Artificial Sequence
<220> FEATURE:
<223> OTHER INFORMATION: primer SKES-1

<400> SEQUENCE: 21
ggaagccacg caaagctgca actcagg                                   27

<210> SEQ ID NO 22
<211> LENGTH: 24
<212> TYPE: DNA
<213> ORGANISM: Artificial Sequence
<220> FEATURE:
<223> OTHER INFORMATION: primer SKES-2.45

<400> SEQUENCE: 22
gagttgcagc tttgcgtggc ttcc                                      24

<210> SEQ ID NO 23
<211> LENGTH: 22
<212> TYPE: DNA
<213> ORGANISM: Artificial Sequence
<220> FEATURE:
<223> OTHER INFORMATION: primer SKES2.5

<400> SEQUENCE: 23
ttcagactca gagtcacctt gc                                        22

<210> SEQ ID NO 24
<211> LENGTH: 20
<212> TYPE: DNA
<213> ORGANISM: Artificial Sequence
<220> FEATURE:
<223> OTHER INFORMATION: primer SKES-2

<400> SEQUENCE: 24
accagcagcc ttgcttggcc                                           20

<210> SEQ ID NO 25
<211> LENGTH: 22
<212> TYPE: DNA
<213> ORGANISM: Artificial Sequence
<220> FEATURE:

```
<223> OTHER INFORMATION: primer SKES-3

<400> SEQUENCE: 25
catgccagag aagcagggct cc                                        22

<210> SEQ ID NO 26
<211> LENGTH: 22
<212> TYPE: DNA
<213> ORGANISM: Artificial Sequence
<220> FEATURE:
<223> OTHER INFORMATION: final gene specific 5'-RACE primer SKES3.5

<400> SEQUENCE: 26
cgatgatact gtctcttcga gc                                        22

<210> SEQ ID NO 27
<211> LENGTH: 22
<212> TYPE: DNA
<213> ORGANISM: Artificial Sequence
<220> FEATURE:
<223> OTHER INFORMATION: primer SKES-6

<400> SEQUENCE: 27
cctccgcctg ctcatgcctc ag                                        22

<210> SEQ ID NO 28
<211> LENGTH: 29
<212> TYPE: DNA
<213> ORGANISM: Artificial Sequence
<220> FEATURE:
<223> OTHER INFORMATION: primer SKEN-4

<400> SEQUENCE: 28
gtccatcagg agaacttctg tgtcaggat                                 29

<210> SEQ ID NO 29
<211> LENGTH: 21
<212> TYPE: DNA
<213> ORGANISM: Artificial Sequence
<220> FEATURE:
<223> OTHER INFORMATION: final gene specific 5'-RACE primer SKES-4

<400> SEQUENCE: 29
gggaacaagt gcaccatctc c                                         21

<210> SEQ ID NO 30
<211> LENGTH: 29
<212> TYPE: DNA
<213> ORGANISM: Artificial Sequence
<220> FEATURE:
<223> OTHER INFORMATION: primer SKEN-6

<400> SEQUENCE: 30
gctctcatag ggaacaagtg caccatctc                                 29

<210> SEQ ID NO 31
<211> LENGTH: 20
<212> TYPE: DNA
<213> ORGANISM: Artificial Sequence
<220> FEATURE:
<223> OTHER INFORMATION: primer SKES-5

<400> SEQUENCE: 31
cgctcgcatg cacctggtac                                           20
```

<210> SEQ ID NO 32
<211> LENGTH: 22
<212> TYPE: DNA
<213> ORGANISM: Artificial Sequence
<220> FEATURE:
<223> OTHER INFORMATION: primer SKB-1

<400> SEQUENCE: 32
ggagggaatc gagcagctag ag                                              22

<210> SEQ ID NO 33
<211> LENGTH: 26
<212> TYPE: DNA
<213> ORGANISM: Artificial Sequence
<220> FEATURE:
<223> OTHER INFORMATION: primer SKB-2

<400> SEQUENCE: 33
gagcagctaa gggactgttc aaactc                                          26

<210> SEQ ID NO 34
<211> LENGTH: 20
<212> TYPE: DNA
<213> ORGANISM: Artificial Sequence
<220> FEATURE:
<223> OTHER INFORMATION: primer SKB-3

<400> SEQUENCE: 34
ccaggaatgg gattgtccgg                                                 20

<210> SEQ ID NO 35
<211> LENGTH: 22
<212> TYPE: DNA
<213> ORGANISM: Artificial Sequence
<220> FEATURE:
<223> OTHER INFORMATION: primer 3' RACE-2

<400> SEQUENCE: 35
cttggacggc gcttgaggaa cc                                              22

<210> SEQ ID NO 36
<211> LENGTH: 21
<212> TYPE: DNA
<213> ORGANISM: Artificial Sequence
<220> FEATURE:
<223> OTHER INFORMATION: primer 3' RACE-1

<400> SEQUENCE: 36
gcctacaagc cagtgggata g                                               21

<210> SEQ ID NO 37
<211> LENGTH: 21
<212> TYPE: DNA
<213> ORGANISM: Artificial Sequence
<220> FEATURE:
<223> OTHER INFORMATION: primer cDNA-1

<400> SEQUENCE: 37
gccaaggact atctcttgag c                                               21

<210> SEQ ID NO 38
<211> LENGTH: 20
<212> TYPE: DNA
<213> ORGANISM: Artificial Sequence
<220> FEATURE:
<223> OTHER INFORMATION: primer SKB-4

<400> SEQUENCE: 38
ggatggactc gagcactggg						20

<210> SEQ ID NO 39
<211> LENGTH: 22
<212> TYPE: DNA
<213> ORGANISM: Artificial Sequence
<220> FEATURE:
<223> OTHER INFORMATION: primer SKE2.2-4

<400> SEQUENCE: 39
agaggagagt gcagacactt tg					22

<210> SEQ ID NO 40
<211> LENGTH: 23
<212> TYPE: DNA
<213> ORGANISM: Artificial Sequence
<220> FEATURE:
<223> OTHER INFORMATION: primer cDNA-3

<400> SEQUENCE: 40
gaggaccctg acgagatccc aac					23

<210> SEQ ID NO 41
<211> LENGTH: 25
<212> TYPE: DNA
<213> ORGANISM: Artificial Sequence
<220> FEATURE:
<223> OTHER INFORMATION: primer cDNA-9

<400> SEQUENCE: 41
ccatgtgttc ccgtagagtc attcc					25

<210> SEQ ID NO 42
<211> LENGTH: 24
<212> TYPE: DNA
<213> ORGANISM: Artificial Sequence
<220> FEATURE:
<223> OTHER INFORMATION: primer 2.2+SKE-1

<400> SEQUENCE: 42
atggagctcc aagaaggtga catg					24

<210> SEQ ID NO 43
<211> LENGTH: 27
<212> TYPE: DNA
<213> ORGANISM: Artificial Sequence
<220> FEATURE:
<223> OTHER INFORMATION: primer cDNA-5

<400> SEQUENCE: 43
cagaagtgtg gagggaaagc gtctggc					27

<210> SEQ ID NO 44
<211> LENGTH: 24
<212> TYPE: DNA
<213> ORGANISM: Artificial Sequence
<220> FEATURE:
<223> OTHER INFORMATION: primer cDNA-4

<400> SEQUENCE: 44
ccctcagact gttacactca gaac					24

<210> SEQ ID NO 45
<211> LENGTH: 30

```
-continued

<212> TYPE: DNA
<213> ORGANISM: Artificial Sequence
<220> FEATURE:
<223> OTHER INFORMATION: primer cDNA-2

<400> SEQUENCE: 45
cccgttgagc ggaaaacttc ctctcatggc                                           30

<210> SEQ ID NO 46
<211> LENGTH: 25
<212> TYPE: DNA
<213> ORGANISM: Artificial Sequence
<220> FEATURE:
<223> OTHER INFORMATION: primer cDNA-7

<400> SEQUENCE: 46
ggaaaggatt cgtatgtgtc cgtgg                                                25

<210> SEQ ID NO 47
<211> LENGTH: 29
<212> TYPE: DNA
<213> ORGANISM: Artificial Sequence
<220> FEATURE:
<223> OTHER INFORMATION: primer SKEN-5

<400> SEQUENCE: 47
gcaatgcgtt tgctttcttc cagtcatct                                            29

<210> SEQ ID NO 48
<211> LENGTH: 28
<212> TYPE: DNA
<213> ORGANISM: Artificial Sequence
<220> FEATURE:
<223> OTHER INFORMATION: primer cDNA-6

<400> SEQUENCE: 48
gaggagagca gagaagcaat gcgtttgc                                             28

<210> SEQ ID NO 49
<211> LENGTH: 23
<212> TYPE: DNA
<213> ORGANISM: Artificial Sequence
<220> FEATURE:
<223> OTHER INFORMATION: primer cDNA-8

<400> SEQUENCE: 49
gttagagaga aaataaataa ccc                                                  23

<210> SEQ ID NO 50
<211> LENGTH: 22
<212> TYPE: DNA
<213> ORGANISM: Artificial Sequence
<220> FEATURE:
<223> OTHER INFORMATION: primer 2.2+SKE-3

<400> SEQUENCE: 50
ccgtaaacaa caccggatac ac                                                   22
```